(12) United States Patent
Zawada et al.

(10) Patent No.: US 6,288,089 B1
(45) Date of Patent: Sep. 11, 2001

(54) USE OF KINASE INHIBITORS FOR TREATING NEURODEGENERATIVE DISEASES

(76) Inventors: Michael Zawada, 10162 E. Exposition Ave., Denver, CO (US) 80231; Kim Heidenreich, 215 Locust La., Denver, CO (US) 80220; Curt Freed, 9080 E. Jewell Cir., Denver, CO (US) 80231

( * ) Notice: Subject to any disclaimer, the term of this patent is extended or adjusted under 35 U.S.C. 154(b) by 0 days.

(21) Appl. No.: 09/469,980

(22) Filed: Dec. 21, 1999

Related U.S. Application Data

(60) Provisional application No. 60/113,263, filed on Dec. 21, 1998, now abandoned.

(51) Int. Cl.$^7$ .......................... A61K 31/44; A61K 31/505

(52) U.S. Cl. ............................................. 514/341; 514/275

(58) Field of Search ..................................... 514/275, 341

(56) References Cited

U.S. PATENT DOCUMENTS

| | | |
|---|---|---|
| 3,772,441 | 11/1973 | Lombardino . |
| 3,929,807 | 12/1975 | Fitzi . |
| 5,356,917 | 10/1994 | Panetta . |
| 5,656,644 | 8/1997 | Adams et al. . |
| 5,756,499 * | 5/1998 | Adams et al. ..................... 514/235.8 |

FOREIGN PATENT DOCUMENTS

WO 95/03297    2/1995   (WO) .

OTHER PUBLICATIONS

Horstmann et al, Chemical Abstracts, vol. 129, abstract No. 52525, 1998.*
Anderson et al., "DNA Damage and Apoptosis in Alzheimer's Disease: Colocalization with c–Jun Immunoreactivity, Relationship to Brain Area, and Effect of Postmortem Delay," *J. Neurosci.*, 16(5):1710–1719 [1996].
Arai et al., "Evaluation of a 1–methyl–4–phenyl–1,2,3, 6–tetrahydropyridine (MPTP)–treated C57 black mouse model for parkinsonism," *Brain Res.*, 515:57–63 [1990].
Barinaga, "Is apoptosis key in Alzheimer's disease?" *Science* 281:1303–1304 [1998].
Bjorklund et al., "Cross–species neural grafting in a rat model of Parkinson's disease," *Nature* 298:652–654 [1982].
Borasio et al., "A placebo–controlled trial of insulin–like growth factor–I in amyotrophic lateral sclerosis," *Neurology* 51:583–586 [1998].
Butterworth et al., "Trinucleotide (CAG) repeat length is positively correlated with the degree of DNA fragmentation in Huntington's disease striatum," *Neurosci.*, 87:49–53 [1998].
Deacon et al., "Histological evidence of fetal pig neural cell survival after transplantation into a patient with Parkinson's disease," *Nature Med.*, 3:350–353 [1997].

Dunnett and Bjorklund, "Prospects for new restorative and neuroprotective treatments in Parkinson's disease," *Nature* 399 (6738 Suppl):A32–A39 [1999].
Eisen and Weber, "Treatment of Amyotrophic Lateral Sclerosis," *Drugs & Aging* 14(3):173–196 [1999].
Freed et al., "Transplantation of human fetal dopamine cells for Parkinson's disease," *Arch. Neurol.*, 47:505–512 [1990].
Freed et al., "Survival of implanted fetal dopamine cells and neurologic improvement 12 to 46 months after transplantation for Parkinson's disease," *N. Engl. J. Med.*, 327:1549–1555 [1992].
Frisch et al., "A Role of Jun–N–Terminal Kinase in Anoikis; suppression by bcl–2 and crmA," *J. Cell Biol.*, 135:1377–1382 [1996].
Galpern et al., "Xenotransplantation of Porcine Fetal Ventral Mesencephalon in a Rat Model of Parkinson's Disease: Functional Recovery and Graft Morphology," *Exp. Neurol.*, 140:1–13 [1996].
German et al., "The Neurotoxin MPTP Causes Degeneration of Specific Nucleus A8, A9, and A10 Dopaminergic Neurons in the Mouse," *Neurodegeneration* 5:299–312 [1996].
Hagg, "Neurotrophins Prevent Death and Differentially Affect Tyrosine Hydroxylase of Adult Rat Nigrostriatal Neurons in Vivo," *Exp. Neurol.*, 149:183–192 [1998].
Ham et al., "A c–Jun Dominant Negative Mutant Protects Sympathetic Neurons against Programmed Cell Death," *Neuron* 14:927–939 [1995].
Haque et al., "Therapeutic strategies for Huntington's disease based on a molecular understanding of the disorder," *Mol. Med. Today* 3:175–183 [1997].
Heidenreich and Kummer, "Inhibition of p38 mitogen–activated protein kinase by insulin in cultured fetal neurons," *J. Biol. Chem.*, 271:9891–9894 [1996].
Huffaker et al., "Xenografting of fetal pig ventral mesencephalon corrects motor asymmetry in the rate model of Parkinson's disease," *Exp. Brain Res.*, 77:329–336 [1989].
Ichijo et al., "Induction of apoptosis by ASK1, a mammalian MAPKKK that activates SAP/JNK and p38 signaling pathways," *Science* 275:90–94 [1997].
Jackson–Lewis et al., "Time course and morphology of dopaminergic neuronal death caused by the neurotoxin 1–methyl–4–phenyl–1,2,3,6–tetrahydropyridine," *Neurodegeneration* 4(3):257–269 [1995].

(List continued on next page.)

Primary Examiner—William R. A. Jarvis
(74) Attorney, Agent, or Firm—Medlen & Carroll, LLP

(57) ABSTRACT

The present invention relates to methods of treating neurodegenerative diseases, including but not limited to Parkinson's disease. In particular, the present invention provides methods utilizing the administration of pyridyl imidazoles having simultaneous inhibitory activity towards p38 mitogen-activated protein (MAP) kinase and c-jun-N-terminal kinase (JNK). The present invention also provides methods for preventing apoptosis of dopamine neurons using pyridyl imidazoles. The present invention also provides methods for the treatment of neurodegenerative diseases, including but not limited to Parkinson's disease.

15 Claims, 11 Drawing Sheets

OTHER PUBLICATIONS

Kang, "Potential of Gene Therapy for Parkinson's Disease: Neurobiologic Issues and New Developments in Gene Transfer Methodologies," *Mov. Dis.*, 13:59–72 [1998].

Kato et al., "Recent advances in research on neuropathological aspects of familial amyotrophic lateral sclerosis with superoxide dismutase 1 gene mutations: Neuronal Lewy body–like hyaline inclusions and astrocytic hyaline inclusions," *Histol. Histophathol.*, 14:973–989 [1999].

Kawasaki et al., "Activation and involvement of p38 mitogen–activated protein kinase in glutamate–induced apoptosis in rat cerebellar granule cells," *J. Biol. Chem.*, 272: 18518–18521 [1997].

Kim et al., "Alternative cleavage of Alzheimer–associated presenilins during apoptosis by a caspase–3 family protease," *Science* 277:373–376 [1997].

Kitada et al., "Mutations in the parkin gene cause autosomal recessive juvenile parkinsonism," *Nature* 392:605–608 [1998].

Knusel et al., "Selective and Nonselective Stimulation of Central Cholinergic and Dopaminergic Development in vitro by Nerve Growth Factor, Basic Fibroblast Growth Factor, Epidermal Growth Factor, Insulin and the Insulin––like Growth Factors I and II," *Jour. Neurosci.*, 10(2):558–570 [1990].

Kopyov et al., "Safety of Intrastriatal Neurotransplantation for Huntington's Disease Patients," *Exp. Neurol.*, 149:97–108 [1998].

Kummer et al., "Apoptosis induced by withdrawal of trophic factors is mediated by p38 mitogen–activated protein kinase," *J. Biol. Chem.*, 272: 20490–20494 [1997].

Laemmli, "Cleavage of structural proteins during the assembly of the head of bacteriophage T4," *Nature* 227:680–685 [1970].

Langston, "Epidemology Versus Genetics in Parkinson's Disease: Progress in Resolving an Age–old Debate," *Ann. Neurol.*, 44:S45–S52 [1998].

Leroy et al., "The ubiquitin pathway in Parkinson's disease," *Nature* 395:451–452 [1998].

Lindvall, "Neural transplantation: a hope for patients with Parkinson's disease," *NeuroReport* 8(14):iii–x [1997].

Lindvall, "Engineering neurons for Parkinson's disease," *Nature Biotechn.*, 17:635–636 [1999].

Lindvall et al., "Grafts of fetal dopamine neurons survive and improve function in Parkinson's disease," *Science* 247:574–577 [1990].

Marsden et al., "An Introduction to the New Surgery for Parkinson's Disease," *Adv. Neurol.*, 74:143–147 [1997].

Marsden and Parkes, "Success and problems of long–term levodopa therapy in Parkinson's disease," *Lancet* 1:345–349 [1977].

Martin, "Neuronal Death in Amyotrophic Lateral Sclerosis is Apoptosis: Possible Contribution of a Programmed Cell Death Mechanism," *J. Neuropathol. Exp. Neurol.*, 58:459–471 [1999].

Mayeux and Sano, "Treatment of Alzheimer 's Disease," *N. Eng. J. Med.*, 341:1670–1679 [1999].

Mizuno et al., "Genetics of Parkinson's disease," *Biomed. Pharmocother.*, 53(3):109–116 [1999].

Mochizuki et al., "Histochemical detection of apoptosis in Parkinson's disease," *J. Neurol. Sci.*, 137:120–123 [1996].

Olanow and Tatton, "Etiology and pathogenesis of Parkinson's disease," *Ann. Rev. Neurosci.*, 22:123–144 [1998].

Olanow et al., "Neural Transplantation as a Therapy for Parkinson's Disease," *Adv. Neurol.*, 74:249–269 [1997].

Olanow et al., "Cell Death and Neuroprotection in Parkinson's Disease," *Ann. Neurol.*, 44:S1–S196 [1998].

Oo et al., "Apoptois in substantia nigra following developmental hypoxic–ischemic injury," *Neuroscience* 69:893–901 [1995].

Oppenheim, "Cell death during development of the nervous system," *Ann. Rev. Neurosci.*, 14:453–501 [1991].

Palfi et al., "Clinical and pathological evaluation of patient with Parkinson's disease (PD) following intracerebroventricular (ICV) GDNF," *Soc. Neurosci. Abstr.*, 24:41 [1998].

Pasinelli et al., "Caspase–1 is activated in neural cells and tissue with amyotrophic lateral sclerosis–associated mutations in copper–zinc superoxide dismutase," *Proc. Natl. Acad. Sci. USA* 95:15763–15768 [1998].

Poewe and Granata, in *Movement Disorders: Neurological Principles and Practice*, Ch. 14 (Watts and Koller [eds]), McGraw–Hill, New York [1997].

Polymeropouos et al., "Mutation in the α–synuclein gene identified in families with Parkinson's disease," *Science* 276:2045–2047 [1997].

Raymon et al., "Application of ex Vivo Gene Therapy in the Treatment of Parkinson's Disease," *Exp. Neurol.*, 144:82–91 [1997].

Riviere et al., "An Analysis of Extended Survival in Patients With Amyotrophic Lateral Sclerosis Treated with Riluzole," *Arch. Neurol.*, 55:526–528 [1998].

Rodriguez, "Subthalamic Nucleus–mediated Excitotoxicity in Parkinson's Disease: A Target for Neuroprotection," *Ann. Neurol.*, 44:S175–S188 [1998].

Rosas et al., "Riluzole Therapy in Huntington's Disease (HD)," *Movement Dis.*, 14:326–330 [1999].

Sasaki et al., "Advanced Glycation End Products in Alzheimer's Disease and Other Neurodegenerative Diseases," *Am. J. Pathol.*, 153:1149–1155 [1998].

Scherzinger et al., "Huntingtin–Encoded Polyglutamine Expansions Form Amyloid–like Protein Aggregates In Vitro and In Vivo," *Cell* 90:549–558 [1997].

Shoulson, "Experimental therapeutics of neurodegenerative disorders: unmet needs," *Science* 282:1072–1074 [1998].

Shoulson et al., "Mortality in DATATOP: A Multicenter Trial in Early Parkison's Disease," *Ann. Neurol.*, 43:318–325 [1998].

Smale et al., "Evidence for Apoptotic Cell Death in Alzheimer's Disease," *Exp. Neurol.*, 133(2):225–230 [1995].

Spencer et al., "Unilateral transplantation of human fetal mesencephalic tissue into the caudate nucleus of patients with Parkinson's disease," *N. Engl. J. Med.*, 327:1541–1548 [1992].

Sramek et al., "Recent Developments in the Drug Treatment of Alzheimer's Disease," *Drugs & Aging* 14:359–373 [1999].

Wadsworth et al., "RWJ 67657, a potent, orally active inhibitor of p38 mitogen–activated protein kinase," *J. Pharmacol. Exp. Ther.*, 291:680–687 [1999].

Wang et al., "Molecular cloning and characterization of a novel p38 mitogen–activated protein kinase," *J. Biol. Chem.*, 272:23668–23674 [1997].

Widner et al., "Bilateral fetal mesencephalic grafting in two patients with parkinsonism induced by 1–methyl–4–phenyl–1,2,3,6–tetrahydropyridine (MPTP)," *N. Engl. J. Med.*, 327:1556–1563 [1992].

Xia et al., "Opposing effects of ERK and JNK–p38 MAP kinases on apoptosis," *Science* 270:1326–1331 [1995].

Zawada et al., "Somatic cell cloned transgenic bovine neurons for transplantation in parkinsonian rats" *Nature Medicine* 4:569–573 [1998].

Zawada et al., "Apoptosis induced by serum withdrawal in embryonic mesencephalic cultures is mediated by p38 MAP kinase," Society for Neuroscience 27th Annual Meeting, New Orleans, LA, vol. 23, Abstract No. 881.13 [Oct. 25–30, 1997].

Cuenda et al., "SB 203580 is a specific inhibitor of a MAP kinase homologue which is stimulated by cellular stresses and interleukin–1," *FEBS Letters* 364:229–233 [1995].

Gallagher et al., "Regulation of stress–induced cytokine production by pyridinylimidazoles; inhibition of CSBP kinase," *Bioorg. Med. Chem.*, 5(1):49–64 [Jan. 1997].

Jeon et al., "6–Hydroxydopamine lesion of the rat substantia nigra: time course and morphology of cell death," *Neurodegeneration* 4:131–137 [1995].

Lee et al., "A protein kinase involved in the regulation of inflammatory cytokine biosynthesis," *Nature* 372:379–746 [1994].

Tong et al., "A highly speciric inhibitor of human p38 MAP kinase binds in the ATP pocket," *Nature Structural Biol.* 4(4):311–316 [Apr. 1997].

Wilson et al., "The structural basis for specificity of pyridinylimidazole inhibitors of p38 MAP kinase," *Chemistry and Biology* 4(6):423–431 [Jun. 1997].

Gum et al., "Acquisition of Sensitivity of Stress–activated Protein Kinases to the p38 Inhibitor, SB 203580, by Alteration of One of More Amino Acids within the ATP Binding Pocket," *J. Biol. Chem.*, 273(25):15605–15610 [Jun. 19, 1998].

Maroney et al., "Motoneuron apoptosis is blocked by CEP–1347 (KT 7515), a novel inhibitor of the JNK signaling pathway," *J. Neurosci.*, 18:104–111 [Jan. 1, 1998].

Zawada et al., "Growth factors improve immediate survival of embryonic dopamine neurons after transplantation into rats," *Brain Res.*, 786(1–2):96–103 [Mar. 9, 1998].

Bhatt and Ferrell, "The protein kinase p90 Rsk as an essential mediator of cytostatic factor activity," *Science* 286:1362–1365 [1999].

Bonni et al., "Cell survival promoted by the RAS–MAPK signaling pathway by transcription–dependent and –independent mechanisms," *Science* 286:1358–1362 [1999].

Gross et al., "Induction of metaphase arrest in cleaving Xenopus embryos by the protein kinase p90$^{Rsk}$," *Science* 286:1365:1367 [1999].

Lee et al., "p38 mitogen–activated protein kinase inhibitors—mechanisms and therapeutic potentials," *Pharmacol. Ther.*, 82:389–397 [1999].

Liverton et al., "Design and synthesis of potent, selective, and orally bioavailable tetrasubsituted imidazole inhibitors of p38 mitogen–activated protein kinase," *J. Med. Chem.*, 42(12):2180–2190 [1999].

Mendis et al., "Management of Parkinson's disease a review of current and new therapies," *Can. J. Neurol. Sci.*, 26(2):89–103 [1999].

Nebreda and Gavin, "Cell survival demands some Rsk," *Science* 286:1309–1310 [1999].

Tibbles and Woodgett, "The stress–activated protein kinase pathways," *Cell Mol. Life Sci.*, 55(10):1230–1254 [1999].

Horstmann et al., "Inhibitors of p38 Mitogen–Activated Protein Kinase Promote Neuronal Survival In Vitro," *Journal of Neuroscience Research* 52:483–490 [May 15, 1998].

Meintzer et al., "Inhibitors of p38 MAP kinase block neuronal apoptosis," The Endocrine Society, 80th Annual Meeting, Oral Session 37, Abstract No. OR37–4, New Orleans, LA [Jun. 24–27, 1998].

Sable et al., "Regulation of apoptosis in rat cerebellar granule neurons," The Endocrine Society, 81st Annual Meeting, Abstract No. P2–349, San Diego, CA [Jun. 12–15, 1999].

Zawada et al., "Pyridinly imidazole compounds rescue dopaminergic neurons from apoptotic cell death," Society for Neuroscience 29th Annual Meeting, Miami Beach, FL, vol. 25, Abstract No. 801.12 [Oct. 23–28, 1999].

* cited by examiner

USE OF KINASE INHIBITORS FOR TREATING NEURODEGENERATIVE DISEASES

This application claims priority benefit to U.S. Provisional Patent Application No. 60/113,263, filed Dec. 21, 1998, now abandoned.

This invention was made during the course of work supported by the United States Government, under the National Institute of General Medical Sciences (NIGMS) of the National Institutes of Health, Grant Number GM07063, U.S. Public Health Grant Number NS 18639, and a Veterans Affairs Merit Review "02" Award. As such, the United States Government may have certain rights to this invention.

FIELD OF THE INVENTION

This invention relates to methods for treating neurodegenerative diseases (e.g., Parkinson's disease) involving the use of kinase inhibitors.

BACKGROUND OF THE INVENTION

Parkinson's disease is the second most common neurodegenerative disorder, affecting nearly 1 million people in North America. The disease is characterized by symptoms such as muscle rigidity, tremor and bradykinesia.

Early studies of Parkinson's disease showed unusual inclusions in the cytoplasm of neurons (i.e., Lewy bodies), occurring predominantly in the substantia nigra, which innervate the striatal region of the forebrain. Although Lewy bodies were also found in other neurodegenerative conditions, the presence of Lewy bodies in Parkinson's disease is accompanied by cell loss in the substantia nigra. This cell loss is considered to be the defining pathological feature of Parkinson's disease.

Epidemiological studies have reported geographic variation in Parkinson's disease incidence, leading to the search for environmental factors (Olanow and Tatton, Ann. Rev. Neurosci., 22:123–144 [1998]). The recent discovery that 1-methyl-4-phenyl-1,2,3,6-tetrahydropyridine (MPTP) toxin causes a Parkinson's-like syndrome indistinguishable from the idiopathic disease suggests that Parkinson's disease may be caused by environmental factors (e.g., toxins and causative agents). (See e.g., Langston, Ann. Neurol., 44:S45–S52 [1998]).

Recent research has also identified genes associated with Parkinson's disease (Mizuno et al., Biomed. Pharmacother., 53(3):109–116 [1999]; Dunnett and Bjorklund, Nature 399 (6738 Suppl):A32–A39 [1999]); namely, the α-synuclein gene (Polymeropouos et al., Science 276:2045–2047 [1997]), the parkin gene (Kitada et al., Nature 392:605–608 [1998]), and the UCH-L1 thiol protease gene (Leroy et al., Nature 395:451–452 [1998]). Although additional chromosomal loci associated with the disease state have been identified, these chromosomal loci have not been analyzed at the molecular level. At present, the biochemical roles played by these gene products in both normal cells and in diseased neurons remain ambiguous, and no gene therapy protocols involving their use have been developed.

Furthermore, Parkinson's disease is associated with the progressive loss of dopamine neurons in the ventral mesencephalon of the substantia nigra (Shoulson, Science 282: 1072–1074 [1998]), which innervates the major motor-control center of the forebrain, the striatum. Although a gradual decline in the number of neurons and dopamine content of the basal ganglia is normally associated with increasing age, progressive dopamine loss is pronounced in people suffering from Parkinson's disease, resulting in the appearance of symptoms when about 70–80% of striatal dopamine and 50% of nigral dopamine neurons are lost (Dunnett and Bjorklund, supra). This loss of dopamine-producing neurons resulting in a dopamine deficiency is believed to be responsible for the motor symptoms of Parkinson's disease.

Although the cause of dopaminergic cell death remains unknown, it is believed that dopaminergic cell death is affected by a combination of necrotic and apoptotic cell death. Mechanisms and signals responsible for the progressive degeneration of nigral dopamine neurons in Parkinson's disease have been proposed (Olanow et al., Ann. Neurol., 44:S1–S196 [1998]), and include oxidative stress (from the generation of reactive oxygen species), mitochondrial dysfunction, excitotoxicity, calcium imbalance, inflammatory changes and apoptosis as contributory and interdependent factors in Parkinson's disease neuronal cell death.

Apoptosis (i.e., programmed cell death) plays a fundamental role in the development of the nervous system (Oppenheim, Ann. Rev. Neurosci., 14: 453–501 [1991]), and accelerated apoptosis is believed to underlie many neurodegenerative diseases, including Parkinson's disease (Baringa, Science 281: 1303–1304 [1998]; Mochizuki et al., J. Neurol. Sci., 137: 120–123 [1996]; and Oo et al., Neuroscience 69: 893–901 [1995]). In living systems, apoptotic death can be initiated by a variety of external stimuli, and the biochemical nature of the intracellular apoptosis effectors is at least partially understood.

In light of the selective death of dopamine producing neurons, administration of L-dihydroxyphenylalanine (L-DOPA) remains the most widely used treatment of Parkinson's disease. However, the administration of therapeutically effective doses of L-DOPA is accompanied by disabling side effects. Furthermore, in some cases, treatment with L-DOPA requires the coadministration of a peripheral DOPA-decarboxylase inhibitor (e.g., carbidopa), which is also accompanied by adverse side effects.

Newer drug refinements and developments include direct-acting dopamine agonists, slow-release L-DOPA formulations, inhibitors of the dopamine degrading enzymes catechol-O-methyltransferase (COMT) and monoamine oxidase B (MAO-B), and dopamine transport blockers. These treatments enhance central dopaminergic neurotransmission during the early stages of Parkinson's disease, ameliorate symptoms associated with Parkinson's disease, and temporarily improve the quality of life. However, despite improvements in the use of L-DOPA for treating Parkinson's disease, the benefits accorded by these dopaminergic therapies are temporary, and their efficacy declines with disease progression. In addition, these treatments are accompanied by severe adverse motor and mental effects, most notably dyskinesias at peak dose and "on-off" fluctuations in drug effectiveness (Poewe and Granata, in Movement Disorders. Neurological Principles and Practice (Watts and Koller [eds]) McGraw-Hill, New York [1997]; and Marsden and Parkes, Lancet 1:345–349 [1977]). No drug treatments are currently available that lessen the progressive pace of nigrostriatal degeneration, postpone the onset of illness, or that substantively slow disability (Shoulson, supra).

Other methods for the treatment of Parkinson's disease involve neurosurgical intervention. The thalamic outputs of the basal ganglia are an effective lesion target for the control of tremor (i.e., thalamotomy). Despite the development of modem imaging and surgical techniques to improve the effectiveness of these neurosurgical interventions for the treatment of Parkinson's disease tremor symptoms, the use of neurosurgical therapies is not widely applicable. For example, thalamotomy does not alleviate the akinetic symptoms which are the major functional disability for many people suffering from Parkinson's disease (Marsden et al., Adv. Neurol., 74:143–147 [1997]).

Therapeutic methods aimed at controlling suspected causative factors associated with Parkinson's disease (e.g., therapies which control oxidative stress and excitotoxicity) have also been developed. Clinical trials have shown that administration of antioxidative agents vitamin E and deprenyl provided little or no neuroprotective function (Shoulson et al., Ann. Neurol., 43:318–325 [1998]). Glutamate-receptor blockers and neuronal nitric oxide synthase (NOS) inhibitors have been proposed as therapies for Parkinson's disease, however, no experimental results from human studies have yet been published (Rodriguez, Ann. Neurol., 44:S175–S188 [1998]).

The use of neurotrophic factors to stimulate neuronal repair, survival and growth in Parkinson's disease has also been studied, particularly the use of glial cell line-derived neurotrophic factor (GDNF). Although GDNF protein protects some dopamine neurons from death, it is difficult to supply GDNF protein to the brain. Furthermore, the use of such protein therapies in general is problematic, since protein molecules show rapid in vivo degradation, are unable to penetrate the blood-brain barrier and must be directly injected into the ventricles of the patient's brain (Palfi et al., Soc. Neurosci. Abstr., 24:41 [1998]; Hagg, Exp. Neurol., 149:183–192 [1998]; and Dunnett and Bjorklund, supra). Other neurotrophic factors which may have therapeutic value have been proposed based on in vitro and animal model systems, including neurturin, basic fibroblast growth factor (bFGF), brain-derived neurotrophic factor (BDNF), neurotrophins 3 and 4/5, ciliary neurotrophic factor and transforming growth factor β (TGF-β). However, the effectiveness of these therapies in humans remains unknown. At present, no single chemical compound or peptide has been reported to completely protect dopamine neurons from death by tropic factor withdrawal or neurotoxin exposure.

Cell replacement therapies have also received much attention as potential methods for treating Parkinson's disease (Freed et al., Arch. Neurol., 47:505–512 [1990]; Freed et al., N. Engl. J. Med., 327:1549–1555 [1992]; Lindvall et al., Science 247:574–577 [1990]; Spencer et al., N. Engl. J. Med., 327:1541–1548 [1992]; Widner et al., N. Engl. J. Med., 327:1556–1563 [1992]; Lindvall, NeuroReport 8:iii-x [1997]; Olanow et al., Adv. Neurol., 74:249–269 [1997]; and Lindvall, Nature Biotechn., 17:635–636 [1999]). These neural grafting therapies use dopamine supplied from cells implanted into the striatum as a substitute for nigrostriatal dopaminergic neurons that have been lost due to neurodegeneration. Although animal models and preliminary human clinical studies have shown that cell replacement therapies may be useful in the treatment of Parkinson's disease, the failure of the transplanted neurons to survive in the striatum is a major impediment in the development of cell replacement therapies.

Various sources of dopaminergic neurons for use in the transplantation process have been tried in animal experiments, including the use of mesencephalic dopamine neurons obtained from human embryo cadavers, immature neuronal precursor cells (i.e., neuronal stem cells), dopamine secreting non-neuronal cells, terminally differentiated teratocarcinoma-derived neuronal cell lines (Dunnett and Bjorkland, supra), genetically modified cells (Raymon et al., Exp. Neurol., 144:82–91 [1997]; and Kang, Mov. Dis., 13:59–72 [1998]), cells from cloned embryos (Zawada et al., Nature Medicine 4:569–573 [1998]) and xenogenic cells (Bjorklund et al., Nature 298:652–654 [1982]; Huffaker et al., Exp. Brain Res., 77:329–336 [1989]; Galpem et al., Exp. Neurol., 140:1–13 [1996]; Deacon et al., Nature Med., 3:350–353 [1997]; and Zawada et al., Nature Med., 4:569–573 [1998]). Nonetheless, in current grafting protocols, no more than 5–20% of the transplanted dopamine neurons survive.

As indicated above, currently used therapies are primarily directed at symptomatic relief, are often associated with debilitating side-effects, lose efficacy over time, are difficult to administer to the brain, and provide poor long term management of the disease. In addition, currently used cell replacement therapies involving grafting protocols have not been widely used due to the inability of transplanted cells to survive in the recipient. Thus, new methods for the treatment of Parkinson's disease that are effective and convenient, but lacking in significant side effects are needed. Furthermore, there is a need for methods that improve the viability of endogenous neurons in people suffering from Parkinson's disease. There is also a need for methods that improve the viability of transplanted neurons in patients who have undergone or are undergoing transplantation therapy.

The same considerations are involved in the treatment and management of neurodegenerative diseases other than Parkinson's disease. For example, Parkinson's disease shares many physiological and pathological characteristics with other neurodegenerative disorders, including Alzheimer's disease, Huntington's disease and amyotrophic lateral sclerosis (ALS or Lou Gehrig's disease). In general, these neurodegenerative disorders are progressive (i.e., their symptoms are not apparent until months or more commonly years after the disease has begun), and caused by an initial reduction of neuronal function, followed by a complete loss of function upon neuronal death. In addition, these neurodegenerative disorders are characterized by the presence of protein aggregates that are believed to hamper cellular functions (e.g., neurotransmission), and may ultimately result in cell death (Sasaki et al., Am. J. Pathol., 153:1149–1155 [1998]). Indeed, apoptotic cell death seems to play a significant role in the neurodegenerative process.

Alzheimer's disease is the most common neurodegenerative disorder. Recent experimental evidence suggests that neuronal death in Alzheimer's may occur through apoptosis (Smale et al., Exp. Neurol. 133(2):225–230 [1995]; and Kim et al., Science 277:373–376 [1997]). Furthermore, in the postmortem brains of Alzheimer's patients, expression of the apoptosis-related transcriptional factor c-jun was colocalized within the cells that also contained DNA strand breaks characteristic of apoptosis (Anderson et al., J. Neurosci., 16:1710–1719 [1996]).

Huntington's disease is an autosomal dominant progressive neurodegenerative disorder resulting from a CAG/polyglutamine repeat expansion in the gene encoding this disease, ultimately resulting in the death of striatal neurons. The polyglutamine expansion results in the formation of insoluble, high molecular weight protein aggregates similar to those seen in Alzheimer's disease (Scherzinger et al., Cell 90:549–558 [1997]). Postmortem examination of the brains of patients suffering from Huntington's disease revealed that CAG repeat length positively correlates with the degree of DNA fragmentation within the afflicted striatum (Butterworth et al., Neurosci., 87:49–53 [1998]), indicating that neuronal degeneration observed in Huntington's disease may also occur through an apoptotic process.

Amyotrophic lateral sclerosis (ALS) is caused by a progressive degeneration of spinal cord motor neurons and results in complete paralysis, respiratory depression and death. Aggregates of ubiquitinated proteins have been observed in ALS (Kato et al., Histol. Histopathol., 14:973–989 [1999]). Recent experiments suggest that death of motor neurons in ALS may have an apoptotic component (Pasinelli et al., Proc. Natl. Acad. Sci. USA 95:15763–15768 [1998]; and Martin, J. Neuropathol. Exp. Neurol., 58:459–471 [1999]).

Currently used therapies for Alzheimer's disease, Huntington's disease and amyotrophic lateral sclerosis suffer the same limitations associated with Parkinson's disease therapies described above (See e.g., Sramek et al., Drugs & Aging 14:359–373 [1999]; Mayeux and Sano, N. Eng. J. Med., 341:1670–1679 [1999]; Eisen and Weber, Drugs & Aging, 14:173–196 [1999]; Borasio et al., Neurology 51:583–586 [1998]; Riviere et al., Arch. Neurol., 55:526–528 [1998]; Rosas et al., Movement Dis., 14:326–330 [1999]; Kopyov et al., Exp. Neurol., 149:97–108 [1998]; and Haque et al., Mol. Med. Today 3:175–183 [1997]). These treatments are primarily directed at symptomatic relief, are often associated with severe side-effects, lose efficacy over time, are difficult to administer to the central nervous system, and provide poor long term disease management. Thus, new methods for the treatment of neurodegenerative diseases, including but not limited to Parkinson's disease, Alzheimer's disease, Huntington's disease and amyotrophic lateral sclerosis, that are effective and convenient, but lacking in significant side effects are needed.

SUMMARY OF THE INVENTION

The present invention relates to methods for treating neurodegenerative diseases. In particular, the present invention relates to methods for treating neurodegenerative diseases, comprising the steps of: a) providing a subject suffering from a neurodegenerative disease and a composition comprising a pyridyl imidazole; and b) administering the composition to the subject suffering from neurodegenerative disease under conditions such that neurodegeneration is ameliorated in the subject. In one embodiment, the neurodegenerative disease is selected from the group consisting of Parkinson's disease, Alzheimer's disease, Huntington's disease, and amyotrophic lateral sclerosis. In a preferred embodiment, the neurodegenerative disease is Parkinson's disease. It is not intended that the present invention be limited to any particular stage of the disease (e.g., early or advanced stages).

In one embodiment, the composition is administered to the subject orally. In another embodiment, the composition is a therapeutic composition. In yet another embodiment, the subject is human. In one particularly preferred embodiment, the human is a recipient of transplant cells (i.e., has undergone neuronal cell transplant). In an alternative preferred embodiment, the subject will undergo transplantation of neuronal cells. In yet another preferred embodiment, the composition is administered to a human subject who has transplanted cells, under conditions such that the survival and/or function of the transplanted cells in the subject is improved. In a further preferred embodiment, the composition is a therapeutic composition. In yet another embodiment, the subject is a non-human animal.

In one embodiment, the pyridyl imidazole is selected from the group consisting of PD 169316, isomeric PD 169316, SB 203580, SB 202190, SB 220025, and RWJ 67657. In a preferred embodiment, the pyridyl imidazole is selected from the group consisting of PD 169316 and isomeric PD 169316.

The present invention also provides methods for inhibiting p38 MAP kinase and c-jun-N-terminal kinases, comprising the steps of: a) providing a sample comprising c-jun-N-terminal kinase and p38 kinase and a compound; and b) exposing the sample to the compound under conditions such that the activities of p38 and c-jun-N-terminal kinase are inhibited. In one embodiment, the compound is a pyridyl imidazole. In yet another embodiment, the pyridyl imidazole is selected from the group consisting of PD 169316, isomeric PD 169316, SB 203580, SB 202190, SB 220026, and RWJ 67657. In a preferred embodiment, the pyridyl imidazole is selected from the group consisting of PD 169316 and isomeric PD 169316.

Furthermore, the present invention provides methods of preventing apoptosis of dopamine neurons, comprising the steps of: a) providing dopamine neurons and a composition comprising a pyridyl imidazole; and b) exposing the composition to the dopamine neurons under conditions such that apoptosis of the dopamine neurons is prevented. In a preferred embodiment, the pyridyl imidazole is selected from the group consisting of PD 169316, isomeric PD 169316, SB 203580, SB 202190, SB 220026, and RWJ 67657. In a preferred embodiment, the pyridyl imidazole is selected from the group consisting of PD 169316 and isomeric PD 169316. In one embodiment, the neurons are from an in vitro culture system. In another embodiment, the neurons comprise primary cells. In another embodiment, the neurons are transplanted neurons. In another embodiment, the dopamine neurons are endogenous neurons.

In one embodiment, the methods of the present invention further comprise the step of implanting dopamine neurons to a subject, and wherein the exposing step occurs after the implanting step. In another embodiment, the methods of the present invention further comprise the step of implanting dopamine neurons to a subject, and wherein the exposing step occurs before the implanting step. In yet another embodiment, the methods of the present invention further comprise the step of implanting dopamine neurons to a subject, and wherein the exposing step occurs before and after the implanting step.

DEFINITIONS

To facilitate an understanding of the present invention, a number of terms and phrases are defined below:

As used herein, the term "neurodegeneration" refers broadly to a defect involving or relating to the nervous system. As used herein, the terms "neurodegenerative disorder" or "neurodegenerative disease" refer broadly to disorders or diseases that affect the nervous system, including but are not limited to Parkinson's disease, Alzheimer's disease, Huntington's disease and amyotrophic lateral sclerosis. As used herein, the term "neurodegeneration is reduced" refers to the improvement in the neurodegenerative condition, such that the degree of neurodegeneration is lessened.

As used herein, the term "subject suffering from a neurodegenerative disease" refers to both humans and animals displaying symptoms normally associated with a disease that affects the nervous system. As used herein, the term "animals" refers to all non-human animals. Such non-human animals include, but are not limited to, vertebrates such as rodents (e.g., rats), non-human primates, ovines, bovines, lagomorphs, porcines, caprines, equines, canines, felines, aves, etc.

As used herein, the term "sample" refers broadly to all types of samples obtained from humans and other animals, including but not limited to, body fluids such as urine, blood, fecal matter, cerebrospinal fluid (CSF), semen, and saliva, as well as solid tissue. These examples are not to be construed as limiting the sample types applicable to the present invention.

As used herein, the terms "Parkinson's disease," or "Parkinson's" refer to a neurological syndrome usually resulting from a dopamine deficiency, resulting from degenerative, vascular, or inflammatory changes in the basal ganglia of the substantia nigra. This term also refers to a syndrome which resembles Parkinson's disease, but which may or may not be caused by Parkinson's disease, such as Parkinsonian-like side effects caused by certain antipsychotic drugs.

As used herein, the term "early stage of Parkinson's disease" refers broadly to the first stages in Parkinson's disease, wherein a person suffering from the disease suffers mild symptoms that are not disabling, such as an episodic tremor of a single limb (e.g., the hand), and affect only one side of the body.

As used herein, the term "advanced stage of Parkinson's disease" refers broadly to a more progressive stage in Parkinson's disease, wherein a person suffering from the disease is suffering from symptoms which are typically severe and which may lead to some disability (e.g., tremors encompassing both sides of the body, balance problems, etc.). Symptoms associated with advanced stage Parkinson's disease may vary significantly in individuals, and may take many years to manifest after the initial appearance of the disease.

As used herein, the terms "by oral administration" or "administering orally" refer to the introduction of a pharmaceutical composition into a subject by way of the oral cavity (e.g., in aqueous or solid form).

As used herein, the term "therapeutic composition" refers to a composition that includes a compound in a pharmaceutically acceptable form that prevents and/or reduces the symptoms of a particular disease. In particular embodiments, the term "therapeutic composition" refers to a pharmaceutical composition that prevents and/or reduces the symptoms of a neurodegenerative disorder. It is contemplated that the therapeutic composition of the present invention will be provided in any suitable form. The form of the therapeutic composition will depend on a number of factors, including the mode of administration. For example, a composition for oral administration must be formulated such that the compound remains pharmacologically active following absorption from the gastrointestinal tract. The therapeutic composition may contain diluents, adjuvants and excipients, among other ingredients. In preferred embodiments, the therapeutic compositions of the present invention contain a compound with a inhibitory activity to p38 MAP kinase, and/or a pyridyl imidazole compound.

As used herein, the terms "therapeutic amount," "effective amount," "therapeutically effective amount" and the like refer to that amount of a compound or preparation that successfully prevents or reduces the severity of symptoms associated with a neurodegenerative disease (e.g., Parkinson's disease). It is contemplated that the effective amount of a therapeutic composition will depend on a number of factors, including but not limited to the age, immune status, race, and sex of the subject, and the severity of the disease.

As used herein, the term "pyridyl imidazole" encompasses compounds comprising a pyridine and an imidazole ring, including compounds comprising a substituted pyridine and a substituted imidazole. In preferred embodiments, the pyridyl imidazoles of the present invention encompasses compounds comprising a pyridine substituted with an imidazole ring, and derivatives thereof. Examples of pyridyl imidazole derivatives for use in the methods of the present invention include, but are not limited to PD 169316, isomeric PD 169316, RWJ 67657, SB 203580, SB 202190, SB 220025 (the chemical structures of these compounds are provided below), as well as compounds described in U.S. Pat. No. : 5,656,644 to Adams et al. (hereby incorporated by reference), and isomers and derivatives thereof.

As used herein, the termr "isomer" refers to one of two or more molecules having the same number and kind of atoms and hence the same molecular weight, but differing in respect to the arrangement or configuration of the atoms.

As used herein, the terms "transplant cells" or "transplanted cells" refer broadly to the component (e.g., tissue or cells) being grafted, implanted or transplanted. As used herein, the term "transplantation" refers to the transfer or grafting of tissues or cells from one part of a subject to another part of the same subject, or to another subject, or the introduction of biocompatible materials into or onto the body). As used herein, a transplanted tissue may comprise a collection of cells of identical composition, or derived from an organism (i.e., a donor), or from an in vitro culture (i.e., a tissue culture system).

As used herein, the term "recipient of transplanted cells" refers broadly to the subject undergoing transplantation and receiving transplanted cells.

As used herein, the terms "stress activated protein kinase" or "SAPK" refer to the family of mitogen-activated protein (MAP) kinases which are activated in response to stress stimuli. This MAP kinase family includes, but is not limited to, p38 and c-jun N-terminal kinase (JNK). Stress stimuli may include, but are not limited to, response to toxins, inflammatory cytokines and radiation, and are implicated in apoptosis mechanisms. As used herein, the term "p38 and JNK activities" refer broadly to the activities induced by or associated with p38 and JNK MAP kinases.

As used herein, the term "dopamine neurons" refers broadly to neurons which produce the neurotransmitter dopamine. As used herein, the term "dopamine neurons undergoing apoptosis" refers broadly to a condition of neuronal loss.

As used herein, the terms "tyrosine hydroxylase" or "TH" refers to an enzyme required for dopamine biosynthesis. TH is a commonly accepted marker indicative of dopaminergic neurons in the substantia nigra. As used herein, a TH+ cell is a cell which immunostains positive using an anti-tyrosine hydroxylase primary antibody.

As used herein, the term "cell culture" refers to any in vitro culture of cells, including but not limited to continuous cell lines (e.g., with an immortal phenotype), primary cell cultures, and finite cell lines (e.g., non-transformed cells).

The term "in vitro" refers to an artificial environment and to processes or reactions that occur within an artificial environment. The term "in vivo" refers to the natural environment (e.g., an animal or a cell) and to processes or reactions that occur within a natural environment. The definition of an in vitro versus in vivo system is particular for the system under study. As used herein, an in vitro system refers to studies of cells or processes in an artificial environment, such as in tissue culture vessels and apparatus, whereas study of the same system in an in vivo context refers to the study of cells or processes within an organism, such as a rat or human.

As used herein, the term "primary cell" or "primary culture" refers to a cell or a culture of cells that have been explanted directly from an organism. Primary cultures are neither transformed nor immortal.

As used herein, the term "tissue culture" refers to a collection of techniques for the growth and maintenance of eukaryotic cells in the laboratory. Such techniques may involve tissue culture dishes or other vessels, incubators and sterility containment devices, as known in the art.

As used herein, the term "exogenous" is used interchangeably with the term "heterologous" refer to a substance coming from some source other than its native source. For example, the terms "exogenous protein," or "exogenous cell" refer to a protein or cell from a non-native source, and that have been artificially supplied to a biological system. In contrast, the terms "endogenous protein," or "endogenous cell" refer to a protein or cell that are native to the biological system, species or individual.

BRIEF DESCRIPTION OF THE DRAWINGS

FIGS. 3A–3H show one embodiment of the present invention. In particular.

DESCRIPTION OF THE INVENTION

Figure 1:
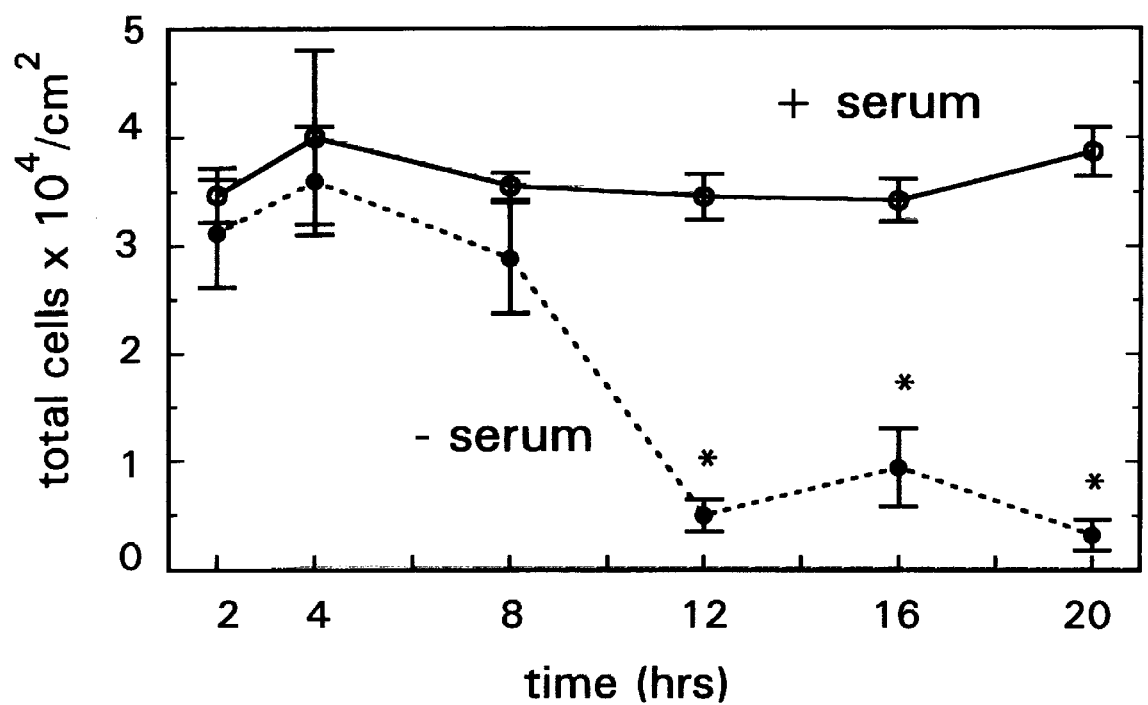
FIG. 1 shows the effect of serum withdrawal on cell survival in a culture of rat ventral mesencephalon primary cells.

The present invention relates to methods of treating neurodegenerative diseases (e.g., Parkinson's disease) by using kinase inhibitors. In particular, the present invention provides methods utilizing the administration of pyridyl imidazoles having an inhibitory activity towards p38 mitogen-activated protein (MAP) kinase. The present invention also provides methods for inhibiting c-jun-N-terminal kinase and for preventing apoptosis of dopamine neurons using pyridyl imidazoles.

For ease in reading, the following Description of the Invention is divided into: I. Experimental Protocols for Testing the Ability of SAPK Inhibitors to Protect Dopamine Neurons; II. Effects of p38 Inhibitors on Cell Survival and Apoptosis; III. Effects of Serum Withdrawal on p38 Levels and Activity; IV. Effects of p38 MAP Kinase Inhibitors on JNK Activity; V. In vivo PD169316-mediated Protection of Transplanted Dopamine Neurons VI. In vitro PD169316-mediated Protection Against 6-OHDA-induced neurotoxicity; VII. Methods for Treating Parkinson's Disease; VIII. Pyridyl Imidazoles and Preparation Thereof; and IX. Formulations and Administration of Compounds.

I. Experimental Groups for Testing the Ability of SAPK Inhibitors to Protect Dopamine Neurons While an understanding of the mechanism is not necessary in order to practice the present invention, recent studies indicate that the stress-activated protein kinase (SAPK), p38 MAP kinase, modulates cellular apoptosis. In some cells, the activity of p38 MAP kinase is stimulated by factors that induce apoptosis including trophic factor withdrawal (Xia et al., Science 270:1326–1331 [1995]; and Kummer et al. J. Biol. Chem., 272:20490–20494 [1997]), excitotoxic stimuli (Kawasaki et al., J. Biol. Chem., 272:18518–18521 [1997]), and Fas activation. Transfection of cells with constitutively-active upstream regulators of p38 MAP kinase induces apoptosis, whereas dominant negative upstream kinases block cell death in response to apoptotic stimuli (Ichijo et al., Science 275: 90–94 [1997]; and Wang et al., J. Biol. Chem., 272:23668–23674 [1997]). Peptide growth factors like insulin that support cell survival block the activity of p38 MAP kinase (Heidenreich and Kummer, J. Biol. Chem,. 271:9891–9894 [1996]). Specific pyridyl imidazole inhibitors of p38 MAP kinase have also been shown to block apoptosis in clonal cell lines in response to trophic factor withdrawal (Kummer et al., J. Biol. Chem. 272: 20490–20494 [1997]) and in primary cerebellar granule neurons in response to cytotoxic stimuli (Kawasaki et al., J. Biol. Chem., 272: 18518–18521 [1997]).

The pyridyl imidazole compounds that inhibit p38 MAP kinase (MAPK) were originally discovered as inhibitors of endotoxin-stimulated cytokine production. While an understanding of the mechanism is not necessary in order to practice the present invention, the inhibitory effect of these compounds toward p38 MAPK is attributed to binding of the drug to the ATP binding pocket of the kinase. The binding of the 4-phenyl ring with specific amino acids in p38 MAP kinase appears to be the major determinant of specificity. One of the pyridyl imidazole compounds, SB 203580, inhibits p38 MAP kinase with an IC50 of 0.6 $\mu$M, and has no effect even at 100 $\mu$M on twelve other protein kinases tested in vitro including the extracellular signal-regulated kinase, ERK2, and the c-jun N-terminus kinase (i.e., JNK).

Although the pyridyl imidazole compounds have been used to explore the specific roles of p38 MAP kinase in a variety of cellular responses in vitro and in animal models of arthritis and endotoxin shock, the effects of pyridyl imidazole compounds on apoptosis of dopamine neurons were never investigated prior to the development of the present invention. It is contemplated that protection of adult dopamine neurons from neurotoxins with SAPK inhibitors will result in the maintenance of normal dopaminergic innervation, although it is not necessary to understand the mechanism of such protection in order to practice the present invention.

The following Tables list experimental groups contemplated for testing the ability of SAPK inhibitors to protect dopamine neurons. Table 1 presents experimental groups contemplated in studies of the protection of dopamine neurons from 6-hydroxydopamine (6-OHDA) toxicity, in a model using partial progressive intrastriatal 6-OHDA lesion in a rat (See Example 9). The following terms are defined, as used in the tables below. Gum tragacanth (Sigma-Aldrich Co.) is a complex mixture of polysaccharides including tragacanthin and bassorin. Gum tragacanth is used as a vehicle for oral administration of drugs in rodents which readily consume the gum. In the context of Tables 1 and 2, the designation "Pharmacological" is used to describe experiments in which pyridyl imidazole compounds are administered to animals to test their protective effects on dopamine neurons in 6-OHDA-induced neurotoxicity (Table 1) and neural transplantation (Table 2) models. The number of surviving TH+ neurons is a measure of the success of these pharmacological experiments. In the context of Tables 1 and 2, the designation "Expression/activation of p38 and JNK" is used to describe experiments designed to measure expression and activity of p38 and JNK in 6-OHDA-lesioned tissue (Table 1) and neural grafts (Table 2) under various treatment paradigms utilizing pyridyl imidazoles. Rat brain lesioning, embryonic mesencephalic tissue transplantation, the TH+ neuronal assay, p38 expression assay and JNK activity assay are all explained in detail in the Examples below.

It is contemplated that in a typical experiment, one hemisphere of a rat brain is lesioned using 6-hydroxydopamine (6-OHDA) neurotoxin by surgical injection into the striatum. 6-OHDA results in the selective killing of dopamine neurons which supply the striatum. The rat brain hemisphere contralateral to the lesioned hemisphere serves as an internal control. Animals receiving SAPK inhibitors are sacrificed one month after 6-OHDA lesion. Brains are perfused with heparinized saline followed by 4% paraformaldehyde, cryopreserved in 30% sucrose solution, and the region of substantia nigra sectioned using a cryostat set at 40 $\mu$m. To identify surviving dopamine neurons, sections are immunostained to detect the presence of tyrosine hydroxylase. All sections in each of the animals are counted, and the final estimate of the number of surviving dopamine neurons is determined using Abercrombie's correction. Furthermore, the effects of SAPK inhibitors on cell survival are also quantitated. Expression and activation of SAPK isozymes are conducted in a separate set of animals, either one or seven days after 6-OHDA injection. Earlier time points are chosen in an attempt to capture the events of unregulated expression and activation of SAPKs following the stress stimulus, although it is not contemplated that the present invention be so limited. Substantia nigra and striatum at the site of 6-OHDA injection are dissected and immediately processed for mRNA and protein expression. A sufficient amount of protein is set aside for immunoprecipitation, western blotting and kinase activity assays.

TABLE 1

| No. of Animals | Treatment | Initiation of Treatment | Type of Experiment |
|---|---|---|---|
| 12 | oral tragacanth for 1 week (control) | 1 day before 6-OHDA | pharmacological |
| 12 | oral tragacanth for 1 week (control) | 1 day after 6-OHDA | pharmacological |
| 12 | oral PD 169316 for 1 week | 1 day before 6-OHDA | pharmacological |
| 12 | oral PD 169316 for 1 week | 1 day after 6-OHDA | pharmacological |
| 12 | oral SB 203580 for 1 week | 1 day before 6-OHDA | pharmacological |
| 12 | oral SB 203580 for 1 week | 1 day after 6-OHDA | pharmacological |
| 12 | intrastriatal saline, sacrifice at 1 day (control) | time 0 for saline | expression/activation of p38 and JNK |
| 12 | intrastriatal 6-OHDA, sacrifice at 1 day | time 0 for 6-OHDA | expression/activation of p38 and JNK |
| 12 | intrastriatal 6-OHDA + best treatment from 1–8, 1 day | time 0 for 6-OHDA, to be determined for the protective treatment | expression/activation of p38 and JNK |
| 12 | intrastriatal saline, sacrifice at 1 week | time 0 for saline | expression/activation of p38 and JNK |
| 12 | intrastriatal 6-OHDA, sacrifice at 1 week | time 0 for 6-OHDA | expression/activation of p38 and JNK |
| 12 | intrastriatal 6-OHDA + best treatment from 1–8, 1 week | time 0 for 6-OHDA, to be determined for protective treatment | expression/activation of p38 and JNK |

Table 2 presents experimental groups contemplated for testing the ability of SAPK inhibitors to protect embryonic dopamine neurons from death following transplantation. It is contemplated that in a typical experiment, unilateral 6-OHDA lesions of the median forebrain bundle and neurotransplantation of embryonic ventral mesencephalon tissue into denervated striatum are performed. For lesioning, 20 $\mu$g of 6-OHDA are injected at two sites in the rat brain. These sites are specific, and are defined by a three-dimensional coordinate system, where a LAT coordinate specifies a position lateral to the midline of the skull or brain, an AP coordinate specifies the anterior-posterior position relative to the bregma (i.e., the point on the skull where the sagittal suture intersects the coronal suture, where the suture in this case is defined as a zone (line) where the bone plates of the skull fuse together) and a VD coordinate specifies the ventral-dorsal range of depth from the dura (i.e., the depth below the thick membrane surrounding the brain). The protocol of these experiments injects and lesions two sites, where the first is defined as AP: −2.1 mm posterior to bregma, LAT: 2.0 mm from the midline, VD: −7.8 mm below the dura; and the second site is defined as AP: −4.3 mm posterior to bregma, LAT: 1.5 mm from the midline, VD: −7.9 mm below the dura. To assess that lesions are complete, animals are intraperitoneally injected with 5.0 mg/kg methamphetamine 7 to 10 days after lesioning. Only animals circling above 3 rpm ipsilateral to the lesion direction are transplanted. Transplantation is performed two to six weeks following lesioning.

For transplantation, ½ of an embryonic ventral mesencephalon is extruded through a 0.2 mm diameter glass extruder into a strand, incubated with either the SAPK inhibitors (10 $\mu$M) or vehicle only for 2 hours at 37° C., and transplanted into the denervated rat striatum. The tissue strand is drawn up into a 24 gauge sterile stainless steel cannula attached to a microliter syringe, and is transplanted at AP: 0.0 mm posterior to bregma, LAT: 3.0 mm from the midline, VD: −3.5 to −7.5 mm below the dura in 4.0 μL over 4 minutes. Some of the transplant recipients receive oral administration of the pyridyl imidizole SAPK inhibitor (60 mg/kg/day for 1 week), while other animals receive transplantation cells that have been preexposed to pyridyl imidizole SAPK inhibitor prior to injection, and still other animals receive both of these treatment regimes.

In other embodiments, it is contemplated that a typical experimental protocol is as follows. Animals are sacrificed one week after transplantation. Brains are paraffin embedded, sectioned at 10 μm, immunostained using anti-tyrosine hydroxylase antibody, and processed for TUNEL staining. Some sections are double stained for tyrosine hydroxylase and cresyl violet to specifically identify apoptotic dopamine neurons. The final estimate of the number of surviving dopamine neurons and TUNEL-positive cells (i.e., apoptotic cells) is made using Abercrombie's correction. Expression and activation of specific SAPK isoforms is studied in tissue cores containing transplanted cells either 24 hours or 1 week after transplantation. The rat brain hemisphere contralateral to the lesioned hemisphere serves as an internal control.

In other experiments, animals are sacrificed 3 months after transplantation. Behavioral improvement measured as a reduction in a circling rate after an intraperitoneal injection of methamphetamine is tested on a monthly basis. After sacrifice at three months following transplantation, the number of surviving dopamine cells is determined using Abercrombie's correction, using 40 μm cryostat sections. The extent of striatal reinnervation is quantitated in coronal brain sections containing transplants immunostained for tyrosine hydroxylase using a Nikon slide scanner. The images are processed and analyzed using NIH Image software. The average area of innervation and its maximal span are calculated for each animal. For behavioral data, repeated measures analysis is conducted in Prism statistical software, with significance defined as $p<0.05$. In some embodiments, these animal studies are done at the University of Colorado USDA approved animal facility in accordance with the University of Colorado IACUC (Institutional Animal Care and Use Committee) protocol #41802098(04)1E. These guidelines are compliant with NIH animal use guidelines

TABLE 2

| No. of Animals | Treatment | Initiation of Treatment | Type of Experiment |
|---|---|---|---|
| 12 | oral tragacanth for 1 week (control) | 1 day before transplantation | pharmacological |
| 12 | preincubation in L-15 medium alone (control) | 2 hours before transplantation | pharmacological |
| 12 | preincubation + oral tragacanth for 1 week (control) | 2 hours + 1 day before transplantation | pharmacological |
| 12 | oral PD 169316 for 1 week | 1 day before transplantation | pharmacological |
| 12 | preincubation in PD 169316 | 2 hours before transplantation | pharmacological |
| 12 | preincubation + oral PD 169316 for 1 week | 2 hours + 1 day before transplantation | pharmacological |
| 12 | oral SB 203580 for 1 week | 1 day before transplantation | pharmacological |
| 12 | preincubation in SB 203580 | 2 hours before transplantation | pharmacological |
| 12 | preincubation + oral SB 203580 for 1 week | 2 hours + 1 day before transplantation | pharmacological |

TABLE 2-continued

| No. of Animals | Treatment | Initiation of Treatment | Type of Experiment |
|---|---|---|---|
| 12 | transplantation, sacrifice at 1 day (control) | N/A | expression/activation of p38 and JNK |
| 12 | transplantation + best Tx from 1–12, 1 day | N/A | expression/activation of p38 and JNK |
| 12 | transplantation, sacrifice at 1 week (control) | N/A | expression/activation of p38 and JNK |
| 12 | transplantation + best Tx from 1–12, 1 week | N/A | expression/activation of p38 and JNK |

Although a rat model system for Parkinson's disease is provided in the present invention, the present invention is not meant to be so limited. It is contemplated that the present invention will encompass any suitable animal model. For example, it is contemplated that practice of the invention encompass the use of MPTP-lesioned mice as a model for Parkinson's disease (Jackson-Lewis et al., Neurodegeneration 4(3):257–269 [1995]; German et al., Neurodegeneration 5:299–312 [1996]; and Arai et al., Brain Res., 515:57–63 [1990]). The mouse model provides the benefits of easy systemic administration of the MPTP, a dopamine neuron-specific neurotoxin, and requires a smaller amount of pyridyl imidazole inhibitor to be administered orally than is required in the rat models.

The objective of the following experiments is to examine if pyridyl imidazole inhibitors can protect nigral dopamine neurons from MPTP-induced death in a mouse model of Parkinson's disease. Mice are injected intraperitoneally with MPTP dissolved in PBS. In the chronic administration protocol, 20 mg/kg of MPTP is injected every 24 hrs for five days. Alternatively, in the acute model, 15 mg/kg of MPTP are injected every 2 hrs for four doses. Control mice receive oral tragacanth gum starting one day before MPTP injection and daily thereafter for one week. Other mice receive oral pyridyl imidazole inhibitors (e.g., PD169316; 60 mg/kg/day) in tragacanth gum starting one day before MPTP injection and daily thereafter for one week. There are 12 mice in each experimental group.

All animals are sacrificed 7 days after the first injection of MPTP. Brains are fixed in 4% paraformaldehyde, cryopreserved in 30% sucrose and the substantia nigra sectioned at 40 μm on a cryostat. Using immunocytochemistry for tyrosine hydroxylase (TH), surviving dopamine neurons are identified and counted under a microscope. It is contemplated that pyridyl imidazole inhibitors will fully or partly protect dopaminergic neurons from MPTP-induced death in the mouse.

As described in more detail below, the present invention provides compositions and methods for increasing neuronal survival in transplants. In particular, the present invention provides methods and compositions to inhibit SAPKs in transplanted tissue. Although it is not necessary to understand the mechanism in order to practice the present invention, and it is not intended that the invention be so limited, it is contemplated that increased neuronal survival in transplants is likely to result in a higher degree of striatal reinnervation, and consequently lead to a more substantial reduction in Parkinsonian symptoms than observed with current transplantation therapy. It is also contemplated that the SAPK inhibitors of the present invention, when admin- II. Effects of p38 Inhibitors on Cell Survival and Apoptosis in Primary Neuronal Cultures Because death of embryonic dopamine neurons in ventral mesencephalic cultures represents a well established model of apoptosis in primary neurons, this system was chosen to study the involvement of p38 MAP kinase in neuronal death. Survival of mesencephalic cultures is dependent on the presence of neurotrophic factors contained in serum. The system utilized E15 rat mesencephalic primary cultures grown in the presence of 5% human placental serum for 24 hours. Complete serum withdrawal at that time led to death of 90% of the cells within 20 hours (See, FIG. 1). FIG. 1 shows the time course of cell death following serum withdrawal in the E15 rat mesencephalic cultures. Cells were grown in F12 defined culture medium supplemented with 5% human placental serum for 24 hours. After that time, the serum-containing medium was replaced with either fresh serum-containing medium or medium lacking serum, and cells were grown for an additional 2–20 hours. At the indicated times, cells were trypsinized and counted using a hemocytometer. The most dramatic cell loss occurred between 8 and 12 hours following serum withdrawal. Data shown in FIG. 1 are presented as the mean ±S.E.M. (n=6, p<0.001). Sister cultures grown in the medium supplemented with serum maintained their cell number at about $3.6 \times 10^4$ cells/cm$^2$ for the entire course of the experiment.

Figure 2:
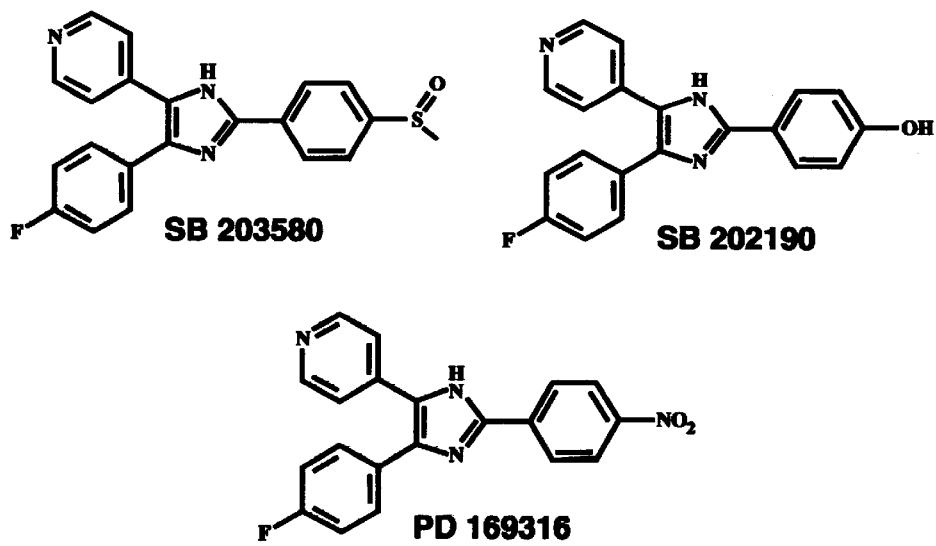
FIGS. 2A and 2B show the effects of various inhibitors of stress-activated protein kinases on the survival of tyrosine hydroxylase (TH)-positive embryonic neurons in the absence of serum.
Figure 2:
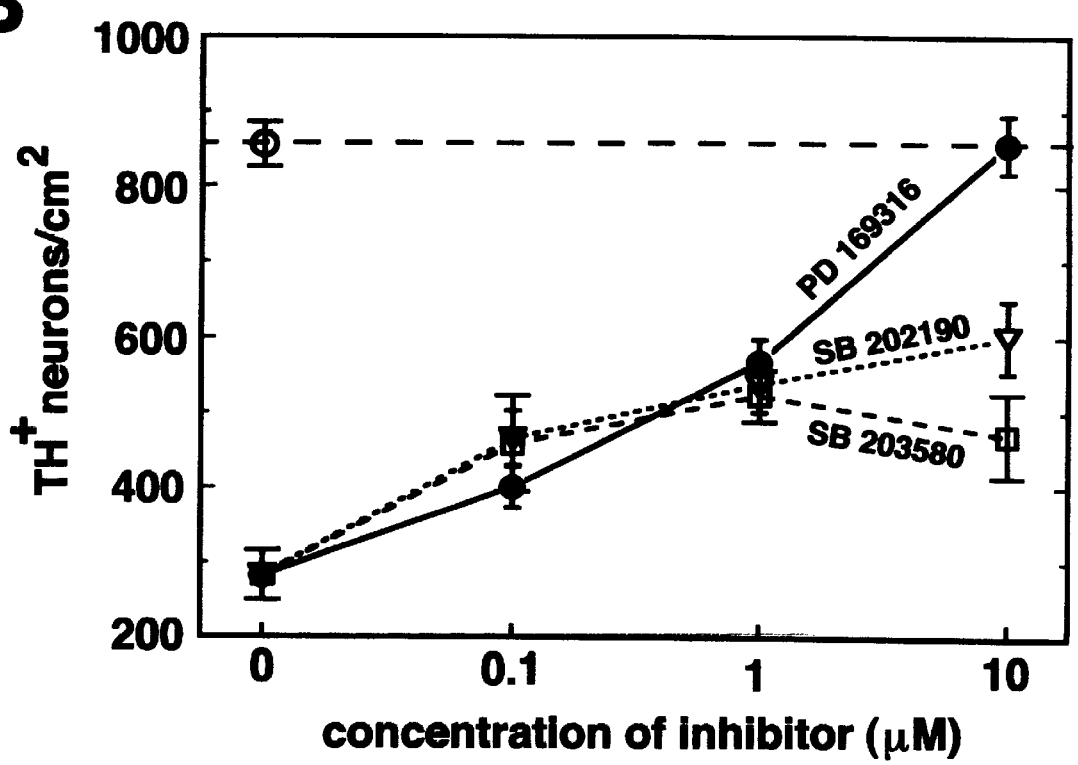

To examine whether p38 plays a role in neuronal apoptosis, the effects of specific p38 inhibitors, SB 203580 and SB 202190, and a putative p38 inhibitor, PD 169316, were studied on apoptosis in these serum-withdrawn cultures. Structures of the pyridyl imidazole compounds are shown in FIG. 2A. The inhibitors differ only by the para substitution in the phenyl ring that is in the 2-position of the imidazole ring. Primary neurons were grown in presence of 5% human placental serum for 24 hours. After that time, medium was replaced with identical medium or medium lacking serum in the presence or absence of p38 inhibitors. Twenty hours after medium change, the cultures were fixed and immunostained for tyrosine hydroxylase (TH) to identify surviving dopamine neurons. In control cultures fed with medium containing serum, there were 856±30 surviving TH+ neurons/cm$^2$ (See, FIG. 2B). This Figure illustrates the protection of dopamine neurons from serum withdrawal-induced death with SAPK inhibitors. Mesencephalic cultures were initially grown for 24 hours in 5% human placental serum. At that time, medium was replaced with an identical medium (open circle) or medium lacking serum in the presence (0.1–10 μM) or absence of SB 203580 (open squares), SB 202190 (open triangles), and PD 169316 (closed circles) for 20 hours. All inhibitors tested at 0.1 and 1.0 μM provided equal protection to dopamine neurons, but at 10 μM, PD 169316 provided highest and complete protection from death by serum withdrawal.

As shown in FIG. 2B, serum withdrawal reduced the number of surviving TH+ neurons/cm$^2$ to 283±32. All p38 inhibitors tested improved survival of TH+ neurons in a dose dependent fashion. The survival effects of SB 203580 and SB 202190 reached their maxima at 1 μM, nearly doubling the number of surviving TH+ neurons. Application of SB 203580 and SB 202190 resulted in survival of 523±34 and 537±37 TH+ neurons/cm$^2$, respectively. The highest dose (i.e., 10 μM) of the SB compounds did not further improve survival of dopamine neurons. In contrast, 10 μM PD 169316 protected all TH+ neurons, supporting survival of 857±39 TH+ neurons/cm$^2$. This experiment also shows that PD 169316 has a unique ability to act as a serum replacement.

To further characterize the involvement of p38 MAP kinase in neuronal apoptosis, PD 169316 was used because it was most efficacious in protecting dopamine neurons in the initial experiment. Twenty hours after media change, dopamine neurons cultured in the presence of serum with or without PD 169316 (10 μM) appeared healthy, and contained long neurites and highly ramified growth cones (See, FIGS. 3A and 3C). In contrast, dopamine neurons from which serum was withdrawn had truncated neurites and lacked growth cones (See, FIG. 3B). Supplementation of the serum-withdrawn cultures with 10 μM PD 169316 restored healthy morphology to the TH+ neurons (See, FIG. 3D). Twenty hours after medium change, the number of dopamine neurons surviving per cm$^2$ in the serum containing cultures was 582±15 while only 60±28 dopamine neurons/cm$^2$ (i.e., 10%) survived serum withdrawal (See, FIG. 4B). Survival of dopamine neurons was improved to 81% of serum controls by 1 μM PD 169316 (p<0.001), while 10 μM inhibitor completely prevented dopamine cell death (p<0.001). The inhibitor had no effects on survival of dopamine neurons in serum containing cultures.

To determine if the survival effects of PD 169316 were restricted to dopamine neurons, the total number of surviving cells under conditions of serum withdrawal was determined. Twenty hours after medium change, the number of cells surviving per cm$^2$ in the serum containing cultures was 28,300±1,204 while only 3,700±973 cells/cm$^2$ (i.e., 13%) survived serum withdrawal (See, FIG. 4A). Cells were grown in defined F12 culture medium containing 5% human placental serum for 24 hours. The medium was subsequently replaced with either the identical medium or medium lacking serum in the presence or absence of various concentrations of PD 169316 (0.1–10 μM). After 20 hours, the experiment was terminated, and total cell survival was estimated. As shown in FIG. 4A, the SAPK inhibitor did not have any significant survival effects on the cells grown in serum. In contrast, in cultures lacking serum, PD 169316 restored the number of surviving cells to that observed in serum controls in a dose-dependent manner. At 1 and 10 μM, the inhibitor improved cell survival to 48% and 80% of serum controls, respectively (p<0.001).

To determine if PD 169316 exerted its survival effects by reducing the rate of apoptosis, the cultures were stained with Hoechst 33258 DNA dye (See, FIGS. 3E–H) and the apoptotic cells were counted (i.e., those containing one or more lobes of condensed nuclear chromatin) (See e.g., FIG. 3F). In the presence of serum, 1.4% of the cells were apoptotic after 20 hours (See, FIG. 4C). The removal of serum increased the number of apoptotic cells to 14%. PD 169316 concentrations of 1 and 10 μM reduced the rate of apoptosis to 3.4% and 1.8%, respectively. The inhibitor had no effect on the basal apoptosis (i.e., 1.4%) observed in cultures supplemented with serum.

The present inventors believed it was important to determine the extent of apoptosis occurring specifically in dopamine cells (i.e., is the apoptosis observed in FIG. 4C equally reflected in the TH+ subpopulation of cells in the culture). To make this determination, select rat embryonic mesencephalic cultures were double stained for both the TH dopaminergic cell marker and for nuclear characteristics indicative of apoptosis. The cell cultures were exposed to either serum-containing or serum-free conditions in the presence or absence on PD169316 (10 μM) and SB203580 (10 μM). Following 18 hrs under these conditions, cultures were immunostained using anti-rat TH primary antibody followed by a fluorescent (FITC-conjugated) secondary antibody. Subsequently, cells were stained with a fluorescent Hoechst 33258 DNA dye. Only those cells containing nuclear chromatin condensations (pyknotic nuclei) were scored as apoptotic. Cells containing intact nuclei -were counted as healthy. In the entire experiment, a total of 5066 TH-immunoreactive neurons were examined for nuclear chromatin condensation. Four sample groups were tested:

1. + serum, n = 2595
2. − serum, n = 269
3. − serum + PD169316, n = 1615
4. − serum + SB203580, n = 587

Figure 5:
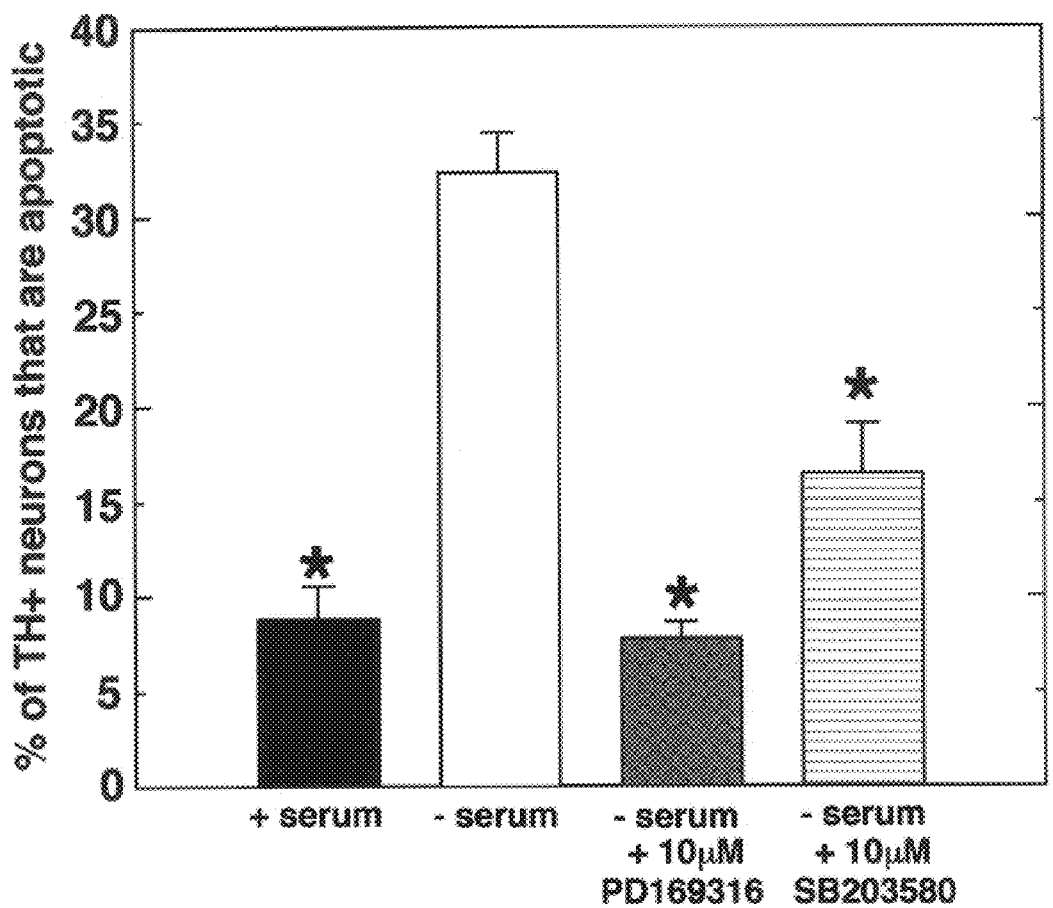
FIG. 5 shows the effects of PD 169316 and SB 203580 in the reduction of percentage of TH+ neurons that are also apoptotic in the absence of serum in a culture of rat ventral mesencephalon primary cells.

The results of this experiment are shown in FIG. 5. In cultures containing serum, only 8.8% dopamine neurons were apoptotic. In contrast, the removal of serum increased the number of apoptotic dopamine neurons to 32.3%. PD169316 fully blocked the increase in the apoptotic nuclear profiles resulting from serum withdrawal ($p<0.001$) and only 7.8% dopamine neurons were apoptotic under this protective treatment. The anti-apoptotic effect of SB203580 was also significant ($p<0.001$), although less dramatic than that of PD169316.

III. Effects of Serum Withdrawal on p38 Levels

Figure 6:
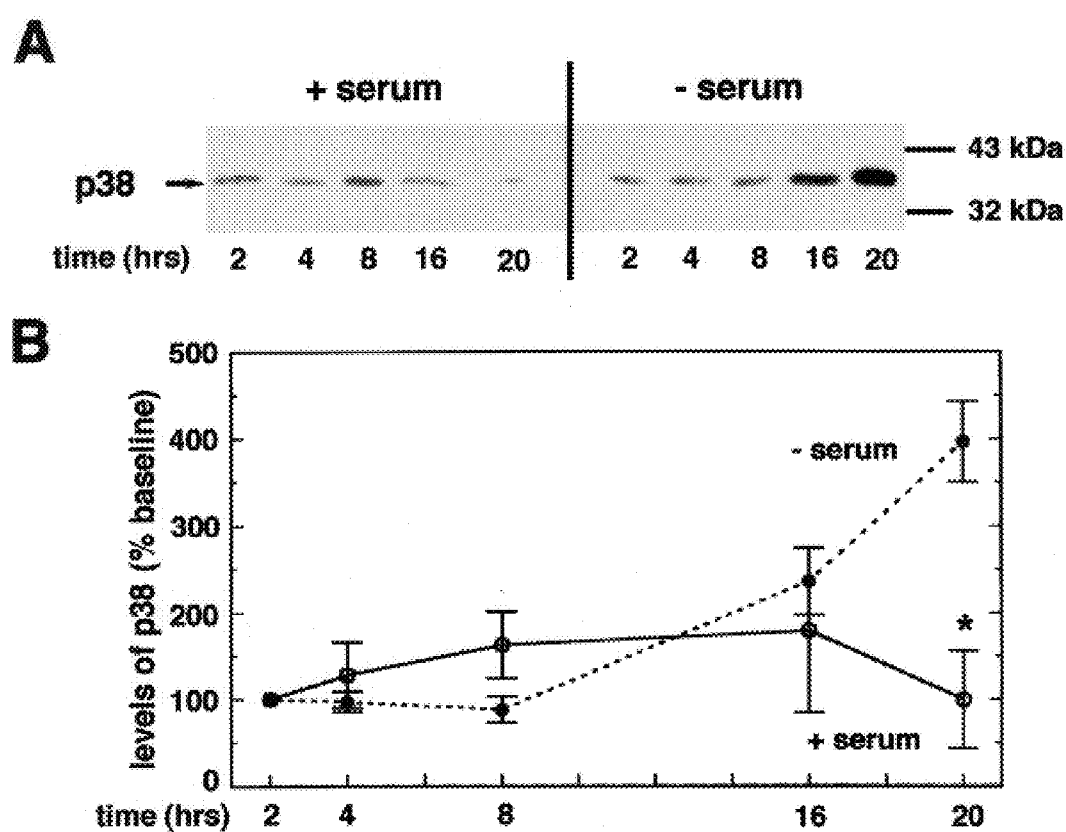
FIG. 6 provides a Western immunoblot illustrating the upregulation of p38 protein levels following serum withdrawal in a culture of rat ventral mesencephalon primary cells.
Figure 7:
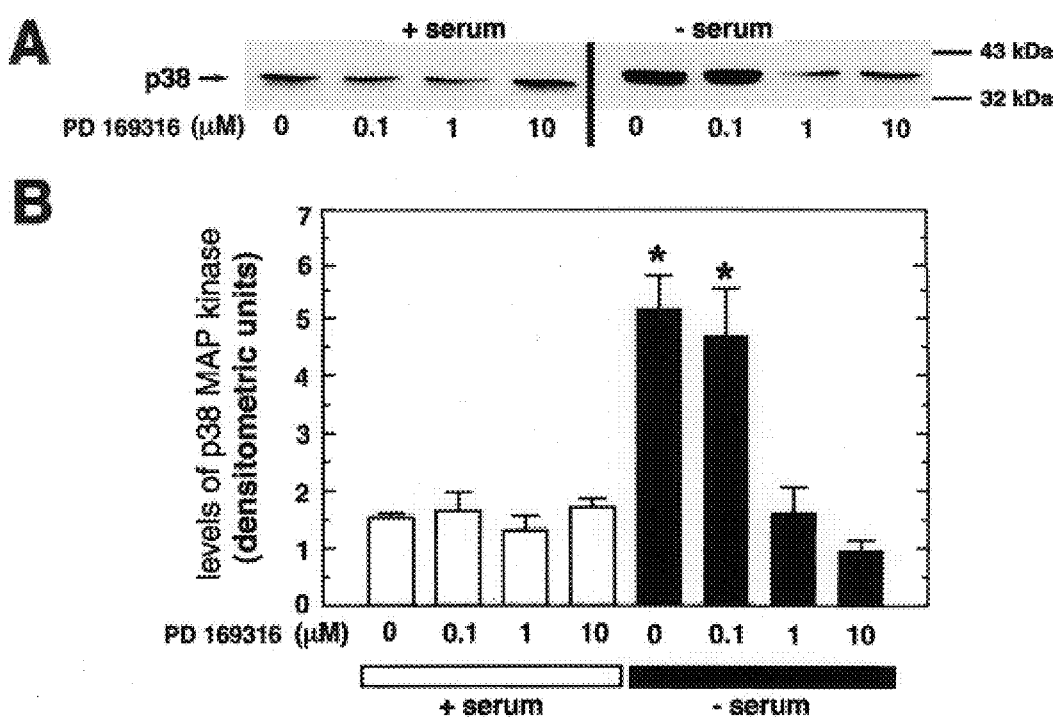
FIG. 7 shows a Western immunoblot illustrating upregulation of p38 protein levels in response to serum withdrawal in a culture of rat ventral mesencephalon primary cells. Furthermore, FIG. 7 also shows the dose dependent effect of PD 169306 concentration on the inhibition of p38 MAP kinase protein induction in the absence of serum.

To determine whether levels of p38 enzyme changed during 20 hours of serum withdrawal, p38 levels were detected using Western immunoblot and an antibody specific to the carboxy terminus of p38. In serum-containing cultures, the level of p38 was unchanged over the 20 hour course of the experiment (See, FIG. 6). In contrast, by 16 hours of serum withdrawal, the levels of p38 reached an apparent but not significant rise to 236±39% of the baseline value. By 20 hours of serum withdrawal, the levels of p38 were significantly elevated above those in serum-containing cultures ($p<0.05$), and reached 397±47% of the baseline value. The increase in the p38 levels observed 20 hours after serum withdrawal was reduced to the baseline value with 1 and 10 $\mu$M PD 169316 (See, FIG. 7). As shown in FIG. 7, the inhibitor (0.1 $\mu$M) did not reduce levels of p38. This low concentration of PD 169316 was also unable to rescue cells from serum-withdrawal induced death.

IV. Effects of p38 MAP Kinase Inhibitors on JNK Activity

Because another stress-activated kinase, JNK, has been implicated as a mediator of apoptosis in some cell types (Xia et al., Science 270: 1326–1331 [1995]; Ham et al., Neuron 14: 927–939 [1995]; and Frisch et al., J. Cell Biol. 135: 1377–1382 [1996]), the mesencephalic cultures were examined for JNK activation and inhibition of JNK by PD 169316.

Figure 8:
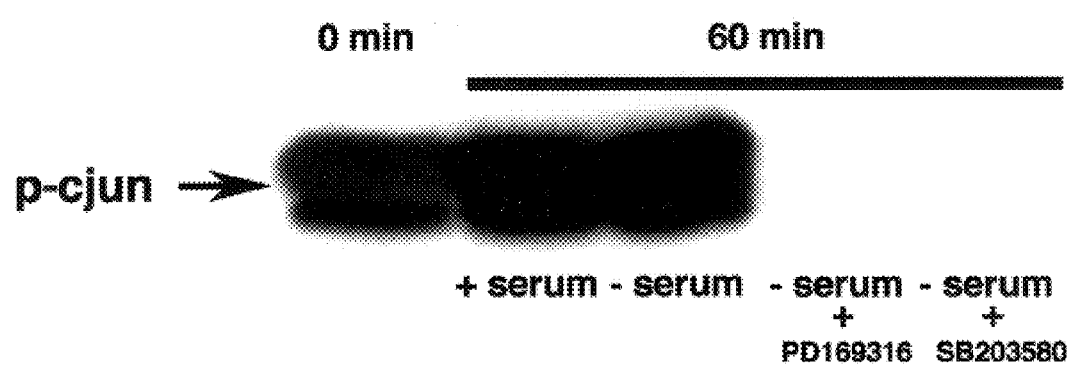
FIG. 8 shows that JNK is constitutively active in embryonic mesencephalic cultures and its activity is reduced by SAPK inhibitors.

JNK was constitutively activated in mesencephalic cultures grown in the presence of serum (See, FIG. 8). JNK activity was not affected during the first hour following serum withdrawal. Addition of PD 169316 (10 $\mu$M) or SB203580 (10 $\mu$M) greatly reduced JNK activity, indicating that primary rat ventral mesencephalic culture contains at least one JNK isoform that is inhibited by pyridyl imidazole compounds (See, FIG. 8). These data indicate that activated JNK, along with p38 MAP kinase, play a role in the induction of the apoptotic response following serum withdrawal. However, it is not necessary to understand the mechanism in order to practice the present invention and it is not intended that the present invention be so limited.

In addition, JNK activity levels were high under basal conditions and changed little following serum withdrawal. Both pyridyl imidazole compounds (PD169316 and SB203580) completely blocked endogenous JNK activity under serum starved conditions. These data suggest that part of the mechanism by which the pyridyl imidazole compounds block apoptosis in dopamine neurons involves inhibition of endogenous JNK activity and prevention of p38 upregulation. However, it is not necessary to understand the mechanism in order to practice the present invention, nor is it intended that the present invention be so limited.

V. In vivo PD169316-Mediated Protection of Transplanted Dopamine Neurons

Figure 9:
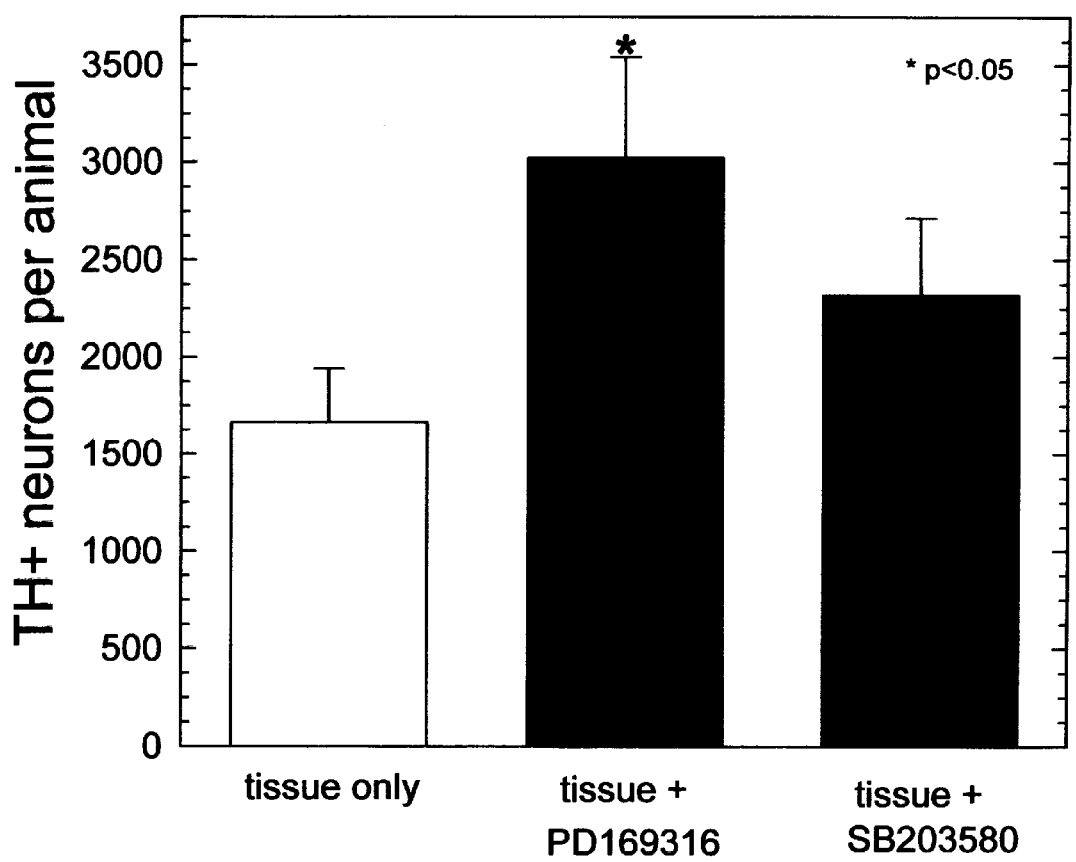
FIG. 9 shows the number of surviving TH+ cells following their transplantation into rat striatum, with or without prior treatment with PD169316 or SB203580.
Figure 10:
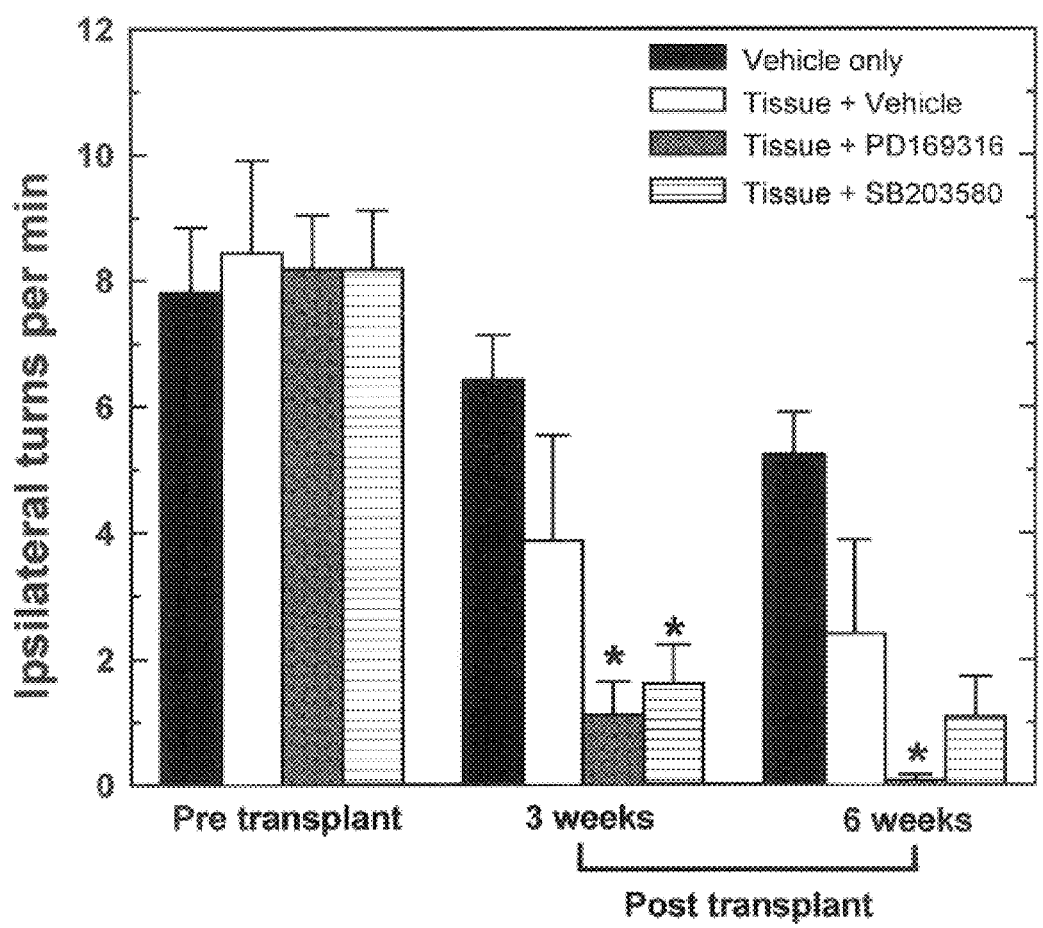
FIG. 10 shows effects of transplanted embryonic neuronal tissue on methamphetamine-induced circling behavior in denervated rats, where the transplanted tissue was either pretreated or not pretreated with PD169316 or SB203580.

The results depicted in FIGS. 9 and 10 demonstrate the in vivo effectiveness of PD169316 and SB203580 in preventing neuronal death of transplanted neurons in a rat model system.

The survival of transplanted rat embryonic mesencephalon tissue pretreated with PD169316 and SB203580 and injected into denervated rat striatum was assayed. In this experiment, rat brain was lesioned by injecting 6-OHDA, resulting in the selective death of dopaminergic neurons which innervate the striatum. After lesioning, the animals received transplants of embryonic rat ventral mesencephalic tissue, which had received one of four treatments:

1. Mock injection of buffer only
2. The tissue was preincubated in buffer;
3. The tissue was preincubated in buffer containing 10 $\mu$M PD169316; or
4. The tissue was preincubated in buffer containing 10 $\mu$M SB203580.

Following the incubation, the tissue was immediately transplanted into the denervated rat striatum. Six weeks after transplantation, TH+ cells within the striatum were visualized following sacrifice of the animals, and cryotome sectioning and immunostaining for tyrosine hydroxylase (TH) using a polyclonal anti-rat TH primary antibody. As shown in FIG. 9, pretreatment of transplanted cells with PD169316 nearly doubled the number of surviving dopamine neurons per animal compared to transplanted tissue that received sham pretreatment with buffer (i.e., the controls). While the PD-treated transplants contained 3023+/−585 surviving dopamine neurons, sham-treated transplants contained only 1662+/−278 surviving dopamine neurons. Transplanted tissue treated with SB203580 contained an intermediate level of TH+ cells.

The ability PD169316 and SB203580 to improve the survival of the transplanted dopaminergic neurons was also assayed. This assay recorded the response of denervated, transplanted rats to methamphetamine exposure. Methamphetamine stimulates dopamine release from both endogenous as well as transplanted dopamine neurons. In the denervated rat, methamphetamine releases dopamine from the intact (i.e., non-denervated) substantia nigra and causes the rat to rotate ipsilateral to (i.e., towards the same side as) the lesion direction (i.e., towards the lesioned side). Following transplantation, dopamine neurons grafted into the denervated striatum will release dopamine following methamphetamine injection, counterbalancing dopamine release from the intact side of the brain, thereby reducing or eliminating ipsilateral circling. The greater the number of dopaminergic neurons re-innervating the striatum, the less profound is the circling behavior in response to methamphetamine. As described above, rat brain was lesioned by injecting 6-OHDA, resulting in the selective death of dopaminergic neurons which innervate the striatum. After lesioning, the animals received transplants of embryonic rat ventral mesencephalic tissue, which had received one of four treatments:

1. Mock injection of buffer only;
2. The tissue was preincubated in buffer;
3. The tissue was preincubated in buffer containing 10 μM PD 169316; or
4. The tissue was preincubated in buffer containing 10 μM SB203580.

Following the incubation, the tissue was immediately transplanted into the denervated rat striatum. At three weeks and six weeks following the transplantation, rats were injected with methamphetamine, which stimulates dopamine release. The methamphetamine-injected animals were placed in an drum apparatus that records the number of rotations per minute (rpm) in the direction toward the side of the brain which received the lesion.

As shown in FIG. 10, transplants of tissue pretreated with PD169316 significantly reduced the rate of circling compared to the transplants of tissue pretreated with buffer only at both three and six weeks after transplantation. At six weeks, PD169316-treated group was the only group to completely stop methamphetamine-induced rotations. The reduction in rotation in the animals receiving tissue pretreated with SB203580 was significantly greater when compared with the animals transplanted with vehicle-treated tissue.

Figure 11:
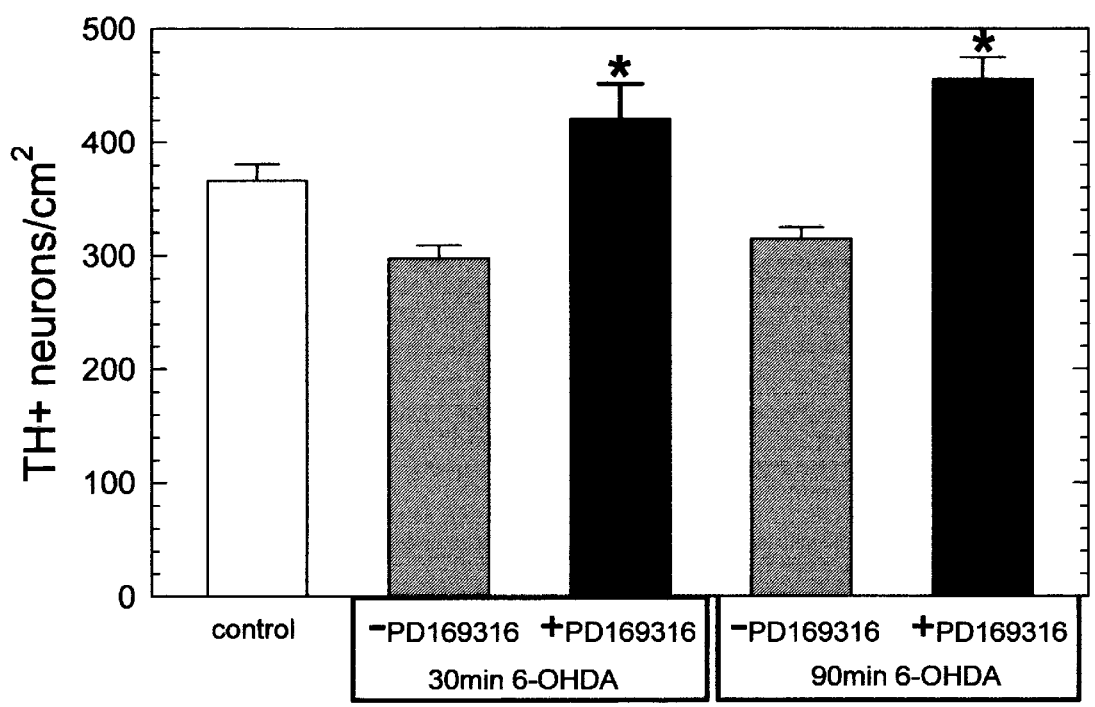
FIG. 11 shows the ability of PD 1693 16 to protect cultured rat embryonic neurons from the neurotoxic effects of 6-OHDA exposure.

VI. In vitro PD169316-Mediated Protection Against 6-OHDA-induced Neurotoxicity This experiment was conducted to determine whether PD169316 can protect cultured dopamine neurons from 6-OHDA-induced cell death. Cultures of embryonic rat mesencephalon were exposed to 50 μM 6-OHDA neurotoxin (RBI) for either 30 or 90 min. Select cultures received a 30-min pretreatment with 10 μM PD169316 prior to 6-OHDA exposure. All cultures were grown for an additional two days in the presence or absence of PD169316. At that time, cultures were screened for TH expression using a polyclonal anti-rat TH antibody and peroxidase-based staining kit. The results of this experiment are shown in FIG. 11. PD169316 fully prevented dopamine cell death caused by 6-OHDA exposure. The effect was equally significant (p<0.001) regardless of the length on the neurotoxin exposure (i.e., 30 or 90 min). This finding demonstrates the in vitro efficacy of PD169316 in protecting cultured primary neurons from 6-OHDA neurotoxicity.

VII. Methods for Treating Neurodegenerative Diseases

As shown above, families of stress-activated protein kinases (e.g., p38 MAP kinase and JNK) mediate serum-withdrawal-induced apoptotic cell death in mesencephalic cultures. Acting as a dual inhibitor, PD 169316 blocks both p38 and JNK pathways, resulting in the complete protection of dopamine neurons from serum withdrawal-induced apoptosis. Furthermore, it was surprising that the administration of a single compound (e.g., PD 169316) resulted in a complete protection of all dopamine neurons. In contrast to other compounds or proteins which only provide a partial protection of dopamine neurons, PD 169316 is shown to protect from 6-OHDA exposure and fully protect 100% of dopamine neurons from death by trophic factor withdrawal. In addition, PD 169316 can be taken orally and readily enters the brain.

Since some neurodegenerative diseases, for example Parkinson's disease, are marked by a progressive loss of dopamine neurons occurring, in part, by an apoptotic mechanism, it is contemplated that the use of p38 MAP kinase and JNK inhibitors will find use in the treatment of neurodegenerative diseases such as Parkinson's disease, although it is not necessary to understand the mechanism in order to practice the present invention, nor is it intended that the present invention be so limited. In particular, p38 MAP kinase and JNK inhibitors (e.g., PD 169316) may be administered to patients suffering from neurodegenerative diseases. For example, such inhibitors may be administered to patients suffering from the early stages of Parkinson's disease, to prevent or reduce the rate of apoptotic cell death (i.e., loss of dopamine neurons). Furthermore, p38 MAP kinase and JNK inhibitors may be administered to Parkinson's disease patients who have undergone, are undergoing or will undergo fetal tissue transplant, or other forms of cell replacement therapy, for the improved survival of the transplanted cells. It is contemplated that an inhibitor of both p38 MAP kinase and JNK will be especially effective in preventing or reducing the rate of apoptotic cell death in dopaminergic neurons of neurodegenerative disease patients, such as Parkinson's disease patients. It is further contemplated that an inhibitor of p38 kinase and JNK may be used to treat transplantable neurons prior to their transplantation into a patient with a neurodegenerative disease, such as Parkinson's disease.

VIII. Pyridyl Imidazoles

It is contemplated that the methods of the present invention encompass the use of pyridyl imidazoles having an inhibitory activity towards p38 mitogen-activated protein kinase and JNK. Methods for the preparation of pyridyl imidazoles contemplated for use in the treatment of Parkinson's disease are described in U.S. Pat. No. 5,656,644 to Adams et al., hereby incorporated by reference.

In a preferred embodiment, the methods of the present invention involve the administration of PD 169316 (See, FIG. 2A and Table 3). In yet other preferred embodiments, the methods of the present invention involve the administration of SB 202190, SB 203580, SB 220025 and RWJ 67657 (See, FIG. 2A and Table 3) (See, Wadsworth et al, J. Pharmacol. Exp. Ther., 291: 680–687 [1999]).

TABLE 3

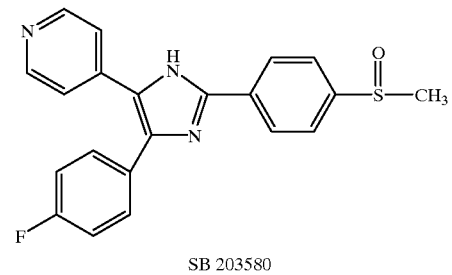

SB 203580

TABLE 3-continued

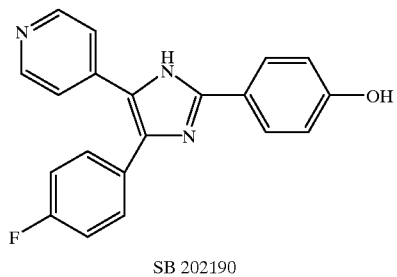

SB 202190

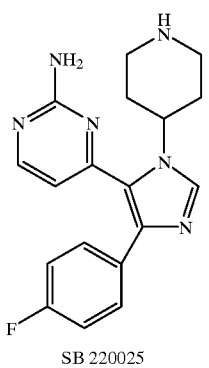

SB 220025

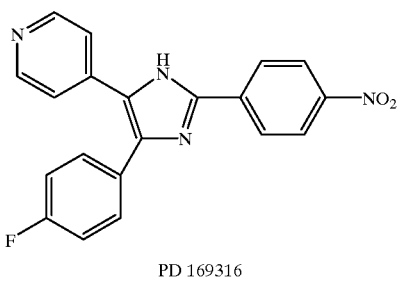

PD 169316

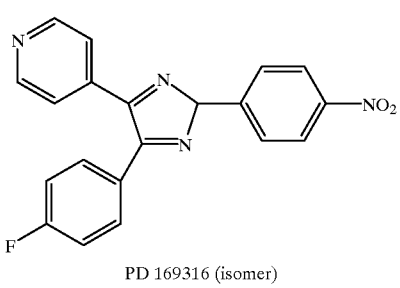

PD 169316 (isomer)

TABLE 3-continued

RWJ 67657

Other pyridyl imidazoles contemplated for use in the methods of the present invention include, but are not limited to:

2-(4-Cyanophenyl)-4-(4-fluorophenyl)-5-(4-pyridyl)-1H-imidazole;

1-Methyl-2-(4-methoxyphenyl)-4-phenyl-5-(4-pyridyl)-imidazole; 2-(4-Cyanophenyl)- 1-methyl-4-phenyl-5-(4-pyridyl)imidazole;

2-(4-Aminomethylphenyl)-1-methyl-4-phenyl-5-(4-pyridyl)-imidazole;

4-[1-Methyl-4-phenyl-5(4-pyridyl)-imidazol-2-yl]benzoic acid, sodium salt;

2-(4-Acetamidomethyphenyl)-1-methyl-4-phenyl-5-(4-pyridyl)imidazole;

Methyl-4-[1-methyl-4-phenyl-5-(4-pyridyl)-imidazol-2-yl]benzoate;

4-(4-Fluorophenyl)-N-1-hydroxy-2-(4-hydroxyphenyl)-5-(4-pyridyl)imidazole;

4-(4-Fluorophenyl)-2-(4-hydroxyphenyl)-5-(4-pyridyl)-1H-imidazole;

4-[4-(4-Fluorophenyl)-5-(4-pyridyl)-1H-imidazol-2-yl]benzoic acid;

2-(4-Cyanophenyl)-4-(4-fluorophenyl)-1-N-hydroxy-5-(4-pyridyl)imidazole;

2-(4-Aminomethylphenyl)-4-(4-fluorophenyl)-5-(4-pyridyl)-1H-imidazole;

2-(4-Cyanophenyl)-4-(4-fluorophenyl)-N-1-hydroxy-5-(4-quinolyl)imidazole;

2-(4-Cyanophenyl)-4-(4-fluorophenyl)-5-(4-quinolyl)-1H-imidazole;

2-(3,5-Dibromo-4-hydroxyphenyl)-4-(4-fluorophenyl)-5-(4-pyridyl)-1H-imidazole;

Ethyl 4-[4-(4-Fluorophenyl)-5-(4-pyridyl)-1H-imidazol-2-yl]-benzoate;

2-[3,5-Dimethyl-4-hydroxy(phenyl)]-4-(4-fluorophenyl)-5-(4-pyridyl)-1H-imidazole;

4-(4-Fluorophenyl-2-(2-hydroxyphenyl)-5-(4-pyridyl)-1H-imidazole;

4-(4-Fluorophenyl)-2-(4-methylthiophenyl)-5-(4-pyridyl)-1H-imidazole; Methyl 4-[4-(4-fluorophenyl)-5-(4-pyridyl)-1H-imidazol-2-yl]-benzoate;

4-(4-Fluorophenyl)-2-(4-methylsulfonylphenyl)-5-(4-pyridyl)-1H-imidazole;

4-(4-Fluorophenyl)-2-(4-methylsulfinylphenyl)-5-(4-pyridyl)-1H-imidazole;

N,N-Dimethyl-4-[4-(4-fluorophenyl-5-(4-pyridyl)-1H-imidazol-2-yl]-benzamide;

2-[(4-N,N-Dimethyl)aminomethylphenyl]-4-(4-fluorophenyl)-5-(4-pyridyl)-1H-imidazole; 2-[4-(Dimethylamiino)phenyl]-4-(4-fluorophenyl)-5-(4-pyridyl)-1H-imidazole;

4-(4-Fluorophenyl)-2-phenyl-5-(4-pyridyl)-1H-imidazole;

2-[4-(2-Dimethylaminopropoxy)phenyl]-4-(4-fluorophenyl)-5-(4-pyridyl)-1H-imidazole;

4-(4-Fluorophenyl)-2-(4-nitrophenyl)-5-(4-pyridyl)-1H-imidazole;

N,N-Dimethyl-4-[2-(4-fluorophenyl)-5-(4-pyridyl)-1H-imidazol-2-yl]benzoyloxyacetamide;

2-(4-Aminophenyl)-4-(4-fluorophenyl)-5-(4-pyridyl)-1H-imidazole; 4-(4-Fluorophenyl)-2-(4-methanesulfonamidophenyl)-5-(4-pyridyl)-1H-imidazole;

4-[4-(4-Fluorophenyl)-5-(4-pyridyl)-1H-imidazol-2-yl]phenyl-sulfonamide;

N'-Cyano-N-4-[(fluorophenyl)-5-(4-pyridyl)-1H-imidazol-2-yl]benzylguanidine;

2-[4-(Methanesulfonamido)methylphenyl]-4-(4-fluorophenyl)-5-(4-pyridyl)-1H-imidazole; 4-(4-Fluorophenyl)-2-(4-methoxyphenyl)-5-(4-pyridyl)-1H-imidazole;

2-(4-Amino-3-iodophenyl)-4-(4-fluorophenyl)-5-(4-pyridyl)-1H-imidazole;

N-Benzyl-N-methyl-4-[4-(4-fluorophenyl-5-(4-pyridyl)-1H-imidazol-2-yl]benzamide;

2-[4-(N-Benzyl-N-methyl)aminomethylphenyl]-4-(4-fluorophenyl)-5-(4-pyridyl)- 1H-imidazole; 4-(4-Fluorophenyl)-N-1-hydroxy-2-(4-methylthiophenyl)-5-(4-quinolyl)imidazole; 4-(4-Fluorophenyl)-2-(4-methylthiophenyl)-5-(4-quinolyl)-1H-imidazole;

4-(4-Fluorophenyl)-2-(4-methylsulfinylphenyl)-5-(4-quinolyl)-1H-imidazole;

4-(3-Chlorophenyl)-2-(4-methylsulfinylphenyl)-5-(4-pyridyl)-1H-imidazole;

4-(3-Chlorophenyl)-N-1-hydroxy-2-(4-methylthiophenyl)-5-(4-pyridyl)-1H-imidazole;

4-(3-Chlorophenyl)-2-(4-methylthiophenyl)-5-(4-pyridyl)-1H-imidazole;

4-(4-Fluorophenyl)-2-(4-formamidomethylphenyl)-5-(4-pyridyl)-1H-imidazole;

4-[4-(4-Fluorophenyl)-5-(4-pyridyl)-1H-imidazol-2-yl]-benzohydroxamic acid;

O-Benzyl-4-[4-(4-Fluorophenyl)-5-(4-pyridyl)-1H-imidazol-2-yl]-benzohydroxamic acid; 4-[4-(4-Fluorophenyl)-5-(4-pyridyl)-1H-imidazol-2-yl]benzamidoxime;

N"-Methyl-N'-cyano-N-[4-(4-fluorophenyl)-5-(4-pyridyl)-1H-imidazol-2-yl]-benzylguanidine;

N-1-Hydroxy-4-(3-methoxyphenyl)-2-(4-methylthiophenyl)-5-(4-pyridyl)-1H-imidazole;

4-(3-Methoxyphenyl)-2-(4-methylthiophenyl)-5-(4-pyridyl)imidazole;

4-(3-Methoxyphenyl)-2-(4-methylsulfinylphenyl)-5-(4-pyridyl)-1H-imidazole;

Morpholino-4-[4-(4-fluorophenyl)-5-(4-pyridyl)-1H-imidazol-2-yl]benzamide;

4-(4-Fluorophenyl)-5-[4-(2-methylpyridyl)]-2-(4-methylthiophenyl)-1H-imidazole;

4-(4-Fluorophenyl)-5-[4-(2-methylpyridyl)]-2-(4-methylsulfinylphenyl)-1H-imidazole;

4-(4-Fluorophenyl)-N-1-hydroxy-5-(4-pyrimidinyl)-imidazole;

4-(4-Fluorophenyl)-2-(4-methylthiophenyl)-5-(4-pyrimidinyl)-1H-imidazole;

4-(4-Fluorophenyl)-2-(4-methylsulfinylphenyl)-5-(4-pyrimidinyl)-1H-imidazole;

4-(4-Fluorophenyl)-2-(4-methylsulfonylphenyl)-5-(4-pyrimidinyl)-1H-imidazole;

4-(4-Fluorophenyl)-2-(4-Morpholinomethylphenyl)-5-(4-pyridyl)-1H-imidazole;

4-(4-Fluorophenyl)-2-(4-hydroxymethyl)-5-(4-pyridyl)-1H-imidazole;

4-[4-(4-Fluorophenyl)-5-(4-pyridyl)-1H-imidazol-2-yl]-benzaldehyde;

4-(2-Methoxyphenyl)-2-(4-methylsulfinylphenyl)-5-(4-pyridyl)-1H-imidazole;

N-1-Hydroxy-4-(2-methoxyphenyl)-2-(4-methylthiophenyl)-5-(4-pyridyl)imidazole;

4-(2-Methoxyphenyl)-2-(4-methylthiophenyl)-5-(4-pyridyl)-1H-imidazole;

3-[4-(4-Fluorophenyl)-5-(4-pyridyl)-1H-imidazol-2-yl]phenyl-5-methyl-4,5-dihydro-4-oxadiazole; 3-[4-(4-Fluorophenyl)-5-(4-pyridyl)-1H-imidazol-2-yl]phenyl-5-methyl-1,2,4-oxadiazole; 4-(3-Aminophenyl)-2-(4-methylthiophenyl)-5-(4-pyridyl)-1H-imidazole;

N-1-Hydroxy-2-(4-methylthiophenyl)-4-(3-nitrophenyl)-5-(4-pyridyl)imidazole;

2-(4-Methylthiophenyl)-4-(3-nitrophenyl)-5-(4-pyridyl)-1H-imidazole;

4-(3-Methanesulfonamidophenyl)-2-(4-methylthiophenyl)-5-(4-pyridyl)-1H-imidazole;

3-[4-(4-Fluorophenyl)-5-(4-pyridyl)-1H-imidazol-2-yl]phenyl-1,2,4-oxadiazol-5-(4H)-one; 4-(3-Acetamidophenyl)-2-(4-methylthiophenyl)-5-(4-pyridyl)-1H-imidazole;

4-(4-Fluorophenyl)-1-N-hydroxy-5-[4-(2-methylpyridyl)]-2-(4-methylthiophenyl)-imidazole;

3-[4-(4-Fluorophenyl)-5-(4-pyridyl)1H-imidazol-2-yl]-phenyl-5,5-dimethyl-4,5-dihydro -1,2,4-oxadiazole;

N-Hydroxy-N-1-[4-[4-(4-fluorophenyl)5-(4-pyridyl)-1H-imidazol-2-yl]phenyl]-ethylurea;

N-Hydroxy-N-[4-[4-(4-fluorophenyl)-5-(4-pyridyl)-1H-imidazol-2-yl]phenyl]-methyl urea;

4-(3-Methylthiophenyl)-2-(4-morpholinomethylphenyl)-5-(4-pyridyl)-1H-imidazole;

4-(3-Methylsulfinylphenyl)-2-(4-morpholinomethylphenyl)-5-(4-pyridyl)-1H-imidazole;

4-(3-Methanesulfonamidophenyl)-2-(4-methylsulfinylphenyl)-5-(4-pyridyl)-1H-imidazole
2-(4-Ethylthiophenyl)-4-(4-fluorophenyl)-5-(4-pyridyl)-1H-imidazole;
2-(4-Ethylsulfinylphenyl)-4-(4-fluorophenyl)-5-(4-pyridyl)-1H-imidazole;
4-(4-Fluorophenyl)-2-[(4-(4-methyl-1-piperzinyl)-sulfonyl-phenyl]-5-(4-pyridyl)-1H-imidazole; 4-(4-Fluorophenyl)-2-[4-(N-methylmethanesulfonamido)-methylphenyl]-5-(4-pyridyl)-1H-imidazole;
Diethyl-[1-methyl-4-phenyl-5-(4-pyridyl)-imidazol-2-yl]methoxy]methylphosphonate;
4-(4-Fluorophenyl)-2-(4-methylthiophenyl)-5-(4-pyridyl)-1H-imidazole;
4-(4-Fluorophenyl)-2-(3-methylthiophenyl)-5-(4-pyridyl)-1H-imidazole;
4-(4-Fluorophenyl)-2-(3-methylsulfinylphenyl)-5-(4-pyridyl)-1H-imidazole;
4-(4-Fluorophenyl)-2-(4-methoxyphenyl)-5-(4-pyridyl) imidazole;
4-(4-Fluorophenyl)-2-(4-methylsulfinylphenyl)-1-(N-morpholinopropyl)-5-(4-pyridyl) imidazole;
4-(4-Fluorophenyl)-2-(4-methylthiophenyl)-1-(N-morpholinopropyl)-5-(4-pyridyl)-imidazole;
4-(4-Fluorophenyl)-2-(4-methylsulfonylphenyl)-1-(N-morpholinopropyl)-5-(4-pyridyl) imidazole;
4-(4-Fluorophenyl)-1-(methylthio-1-propyl)-2-([4-N-morpholinomethyl]phenyl)-5-(4-pyridyl)imidazole;
4-(4-Fluorophenyl)-1-(methylsulfinyl-1-propyl)-2-([4N-morpholinomethyl]phenyl)-5-(4-pyridyl)imidazole;
4-(4-Fluorophenyl)-1-(methylsulfonyl-1-propyl)-2-([4-N-morpholinomethyl]phenyl)-5-(4-pyridyl)imidazole; and pharmaceutically acceptable salts thereof.

IX. Formulations and Administration of Compounds

As indicated above, the present invention contemplates the use of therapeutic compositions of PD169316, isoforms of PD169316, and other pyridyl imidazoles having an inhibitory activity to p38 mitogen-activated protein kinase in the treatment and prevention of neurodegenerative diseases (e.g., Parkinson's disease). It is not intended that the present invention be limited by the particular nature of the therapeutic preparation. For example, such compositions can be provided together with physiologically tolerable liquid (e.g., saline), gel or solid carriers or vehicles, diluents, adjuvants and excipients, such as pharmaceutical grades of mannitol, lactose, starch, magnesium stearate, sodium saccharin, cellulose, magnesium carbonate, and the like. These compositions typically contain 1%–95% of active ingredient, preferably 2%–70%. In addition, the compositions may contain minor amounts of auxiliary substances such as wetting or emulsifying agents, stabilizing or pH buffering agents or preservatives if desired. The therapeutic compositions contemplated by the present invention are physiologically tolerable and compatible.

These therapeutic preparations can be administered to humans in a manner similar to other therapeutic agents. In general, the dosage required for therapeutic efficacy will vary according to the type of use and mode of administration, as well as the particularized requirements of individual patients. The present invention also contemplates the administration of the therapeutic compositions to other animals for veterinary use, such as domestic animals (e.g., laboratory, companion, exotic and/or livestock animals).

The preferred mode of administration of these preparations depends on several factors, including the stability of the preparation, the bioavailability of the compound following different routes of administration, and the frequency of dosing. A number of oral preparations are commercially available, including tablets, capsules, drops and chewable tablets. The pharmaceutical compositions are composed of one or more pharmaceutically acceptable diluents, excipients or carriers, and are well-known to those skilled in the art (See e.g., U.S. Pat. No. 5,356,917, Panetta). When oral administration is not feasible or when malabsorption is suspected, it is contemplated that the therapeutic compounds of the present invention may be administered systemically through intravenous or intraarterial injection, or by surgical procedure. Using such procedures, the therapeutic compound can be delivered directly to the brain.

Experimental

The following examples are provided in order to demonstrate and further illustrate certain preferred embodiments and aspects of the present invention and are not to be construed as limiting the scope thereof.

In the experimental disclosure which follows, the following abbreviations apply: M (Molar); $\mu$M (micromolar); N (Normal); mol (moles); mmol (millimoles); pmol (micromoles); $\mu$g (grams); mg (milligrams); $\mu$g (micrograms); l or L (liters); ml (milliliters); $\mu$l (microliters); cm (centimeters); mm (millimeters); $\mu$m (micrometers); nm (nanometers); °C. (degrees Centigrade); RT (room temperature); TH antibody (tyrosine hydroxylase antibody; Pel-Freez); HBSS (Hanks' balanced salt solution; Mediatech); F12 medium (Irvince Science); polyethyleneimine (Sigma); ABC staining kit (Vector, Burlingame, Calif.); BSA (bovine serum albumin); EDTA (ethylenediaminetetracetic acid); EGTA (ethylene glycol-bis ($\beta$-aminomethylether)-N,N,N',N'-tetracetic acid); PBS (phosphate buffered saline solution); SDS (sodium dodecyl sulfate); $MgCl_2$ (magnesium chloride); NaCl (sodium chloride); NaOH (sodium hydroxide) $CO_2$ (carbon dioxide); $Ca^{2+}$ (calcium ions); $Mg^{2+}$ (magnesium ions); ATF-2 (activator of transcription, transcription factor protein); SAPK (stress-activated protein kinase); PD 169316 (received as a gift from Alan Saltiel of Parke-Davis Pharmaceuticals, Ann Arbor, Mich.); SB 203580 (Calbiochem); JNK (c-jun-N-terminal kinase); GraphPad (GraphPad, San Diego, Calif.); AP (Anterior/Posterior coordinate); VD (Ventral/Dorsal coordinate); LAT (lateral distance coordinate); hrs and h (hours and hour); min (minutes); Sigma (Sigma-Aldrich Co., St. Louis Mo.); Calbiochem (Calbiochem-NovaChem, La Jolla, Calif.); BioRad (BioRad, Hercules, Calif.); Santa Cruz (Santa Cruz, Santa Cruz, Calif.); Amersham (Amersham, Arlington Heights, Ill.)

EXAMPLE 1

Preparation of Cell Cultures

This Example provides the protocols used during the development of the present invention for the preparation of cell cultures. Primary cultures, derived from E15 rat ventral mesencephalons, were prepared in 1 ml of ice cold $Ca^{2+}/Mg^{2+}$ free Hanks' balanced salt solution (HBSS) by mechanically dispersing tissue pieces using a sterile tip of a 1.0 ml Pipetman, using procedures known in the art (See, Knusel et al., Jour. Neurosci., 10: 558–570 [1990]). Subsequently, cells were centrifuged at 200×g for 5 minutes and resuspended in F12 medium with 5% human placental serum, 2 mM L-glutamine, 100 μg/ml streptomycin, 100 U/ml penicillin, and 2.2 μg/ml ascorbic acid. Human placental serum was dialyzed through dialysis tubing with a 10,000 molecular weight cutoff (Spectrum Medical Industries) in $Ca^{2+}/Mg^{2+}$ containing HBSS for at least 2 hours at room temperature. Cells were seeded onto polyethyleneimine-coated 6-, 24- or 96-well plates (Knusel et al., supra) at a density of $6.0 \times 10^4$ cells/cm$^2$. Cells were grown in a 95% air/5% $CO_2$ humidified atmosphere at 37° C. in serum-containing medium suitable for the growth of the cells as known in the art.

EXAMPLE 2

Cell Morphology Changes and the Prevention of Apoptosis in Mesencephalic Neurons Mediated by PD 169316 in the Presence and Absence of Serum In this Example, the various cell morphology changes associated with treatment with various compounds (e.g., PD 169316), as well as the prevention of apoptosis in mesencephalic neurons in the presence and absence of serum were investigated.

Figure 3:
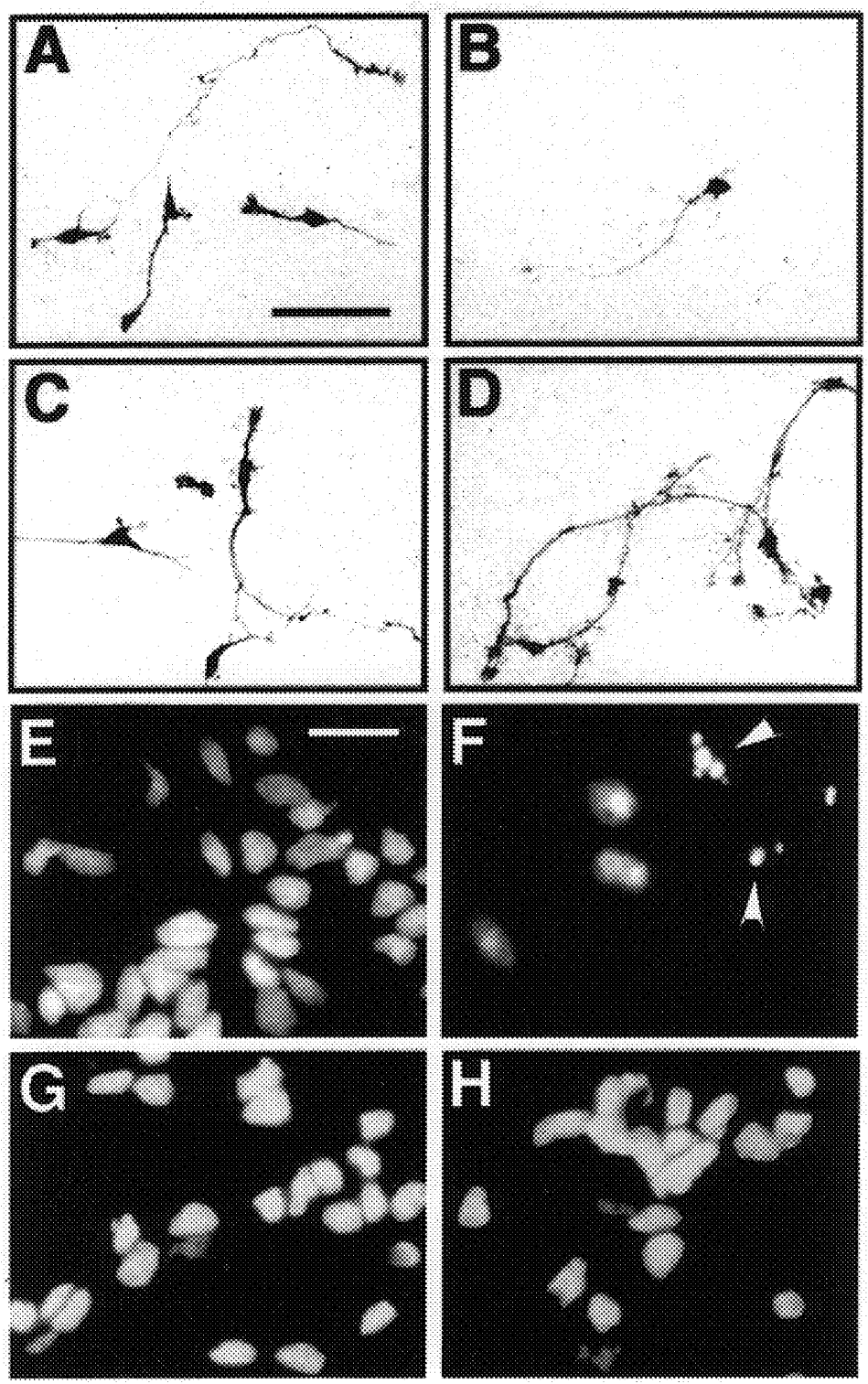
FIG. 3 illustrates cell morphology changes and the prevention of apoptosis in mesencephalic neurons mediated by PD 169316 in the presence or absence of serum.

For example, FIG. 3, Panels A–H illustrate one embodiment of the present invention. Specifically, FIG. 3, Panels A–D provide photomicrographs of embryonic mesencephalic neurons 20 hours following various treatments as described below and in the "Description of the Invention" (scale bar=100 μm). Following these treatments, cells were immunostained using anti-TH antibody and a peroxidase-based visualization system.

FIG. 3A shows neuron cultures in the presence of 5% serum; FIG. 3B shows neuron cultures in the absence of serum; FIG. 3C shows neuron cultures in the presence of 5% serum and 10 μM PD 169316; and FIG. 3D shows neuron cultures in the presence of 10 μM PD 169316 and the absence of serum. The dopamine neurons cultured in the presence of serum with or without PD 169316 (10 μM) appeared healthy, and contained long neurites and highly ramified growth cones (See, FIGS. 3A and 3C). In contrast, dopamine neurons from which serum was withdrawn had truncated neurites and lacked growth cones (FIG. 3B). Supplementation of the serum-withdrawn cultures with 10 μM PD 169316 restored healthy morphology to the TH+ neurons (FIG. 3D).

FIG. 3, Panels E–H provide photomicrographs of embryonic mesencephalic cells 20 hours following various treatments as described below and in the "Description of the Invention" (scale bar in=20 μm). Following the treatments, cells were stained with Hoechst 33258 fluorescent DNA dye to reveal nuclear morphology. FIG. 3E shows mesencephalic cells in the presence of 5% serum; FIG. 3F shows mesencephalic cells in the absence of serum (arrowheads indicate apoptotic nuclei); FIG. 3G shows mesencephalic cells in the presence of 5% serum and 10 μM PD 169316; and Figure H shows mesencephalic cells in the presence of 10 μM PD 169316 and the absence of serum.

To determine whether PD 169316 exerted its survival effects by reducing the rate of apoptosis, the cultures were stained with Hoechst 33258 DNA dye (See, FIGS. 3E–H) and the apoptotic cells (i.e., those containing one or more lobes of condensed nuclear chromatin) were counted. (See e.g., FIG. 3F). In the presence of serum, 1.4% of the cells were apoptotic after 20 hours (See, FIG. 4C). The removal of serum increased the number of apoptotic cells to 14%. Both 1 and 10 μM concentrations of PD 169316 reduced the rate of apoptosis to 3.4% and 1.8%, respectively. The inhibitor had no effect on the basal apoptosis (i.e., 1.4%) observed in cultures supplemented with serum.

EXAMPLE 3

Effects of PD 169316 on Total Cell Survival, Dopamine Neuron Survival and the Rate of Apoptosis in the Presence and Absence of Serum in Mesencephalic Neurons In this Example, experiments were conducted to observe the effects of PD 169316 on cells. Embryonic rat ventral mesencephalon tissue was cultured as described in Example 1, fixed in 4% paraformaldehyde, and stained for tyrosine hydroxylase-immunoreactivity using a polyclonal antibody against rat TH and an ABC staining kit. Following fixation, nonspecific binding was blocked with 10% goat serum in PBS containing 1% BSA and 0.3% Triton-X100 for 60 minutes at room temperature. After rinsing with PBS, a primary rabbit-anti-rat TH antibody (Pel-Freez) (1:200 dilution) was added to each well and allowed to incubate overnight at room temperature. After washing, a biotinylated, affinity-purified, goat anti-rabbit IgG antibody (ABC Kit, Vector) was added to each well and allowed to incubate for 2 hrs at RT. Following washing, an avidin/biotinylated horseradish peroxidase complex (ABC Kit, Vector) was added, and allowed in incubate for 2 hours at room temperature. The peroxidase activity was visualized with diaminobenzidine (DAB) dissolved in PBS and 0.03% hydrogen peroxide. Due to a heterogeneous distribution of the TH-immunoreactive cells in dispersed cell cultures, entire wells were counted. To detect apoptotic cells, adhering cells were stained with Hoechst 33258 DNA dye (8 μg/ml) for 10 minutes, and examined for the presence of nuclear chromatim condensations under a fluorescence microscope. To estimate the total number of surviving cells, cultures were trypsinized and cells were counted using a haemocytometer. The results obtained in one experiment are depicted in FIG. 4.

Figure 4:
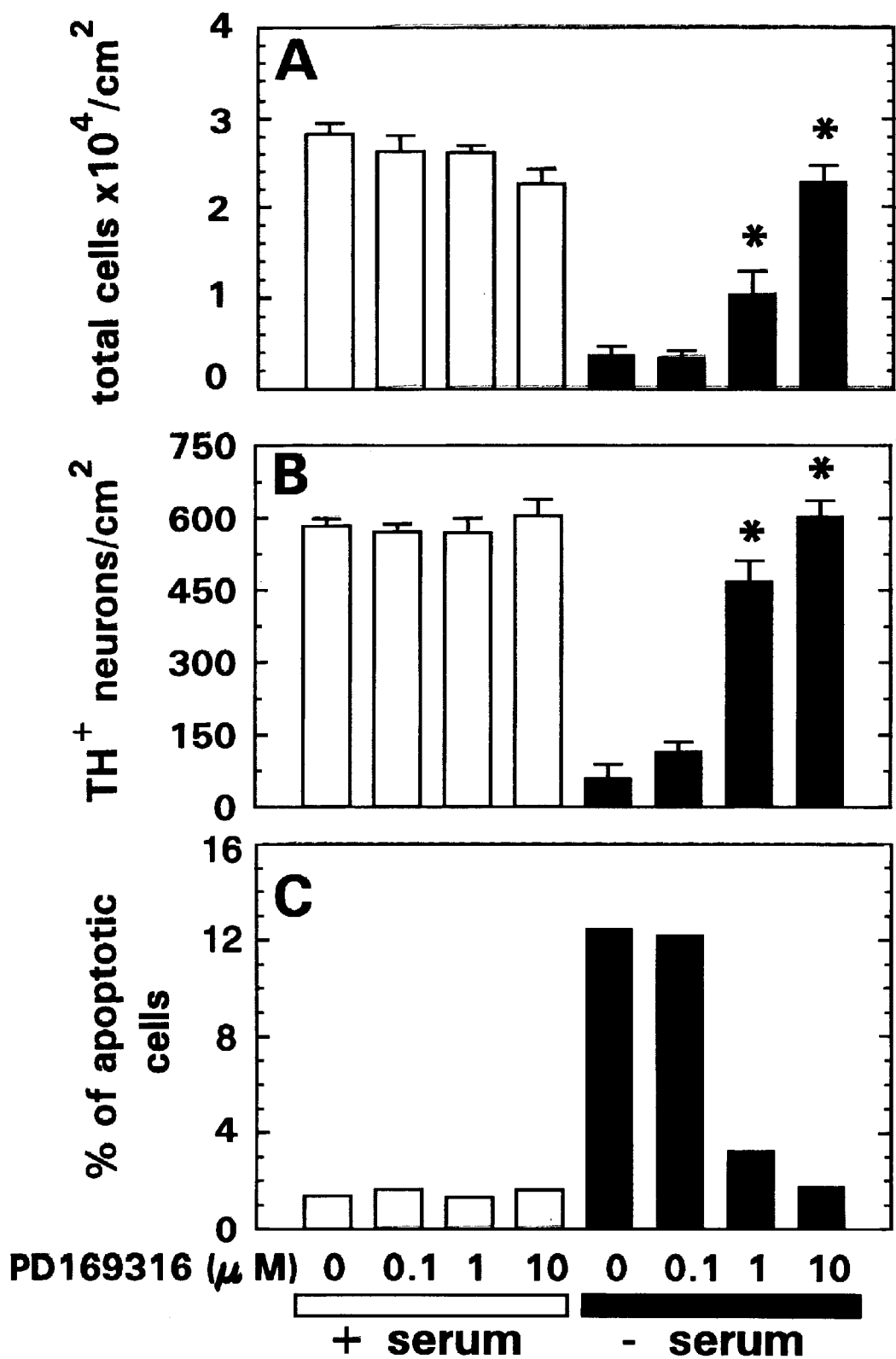
FIGS. 4A–4C show the effects of PD 169316 on total cell survival, dopamine neuron survival and the rate of apoptosis in the presence or absence of serum in a culture of rat ventral mesencephalon primary cells.

FIG. 4 is divided into Panels A–C. FIG. 4, Panels A–C show the effects of PD 169316 on total cell survival, dopamine neuron survival and the rate of apoptosis in the presence or absence of serum in a culture of rat ventral mesencephalon primary cells. Panel A shows the effects of PD 169316 on total cell survival in the absence or presence of serum. As shown in Panel A, PD 169316 protected cells from death by serum withdrawal in a dose-dependent manner (i.e., solid bars), although PD 169316 had no effect on the total cell number in cultures containing serum (i.e., open bars). Panel B shows the effect of PD169316 on survival of TH+ neurons in the presence and absence of serum. As shown in Panel B, the effects of PD 169316 are similar to those observed for the total cell population. Data represents the mean ±S.E.M. (n=6, p<0.001). Panel C shows the effect of PD 169316 on the rate of apoptosis (i.e., percent of adhering apoptotic cells), as determined from counts of at least 400 Hoechst-stained apoptotic nuclei per condition. Apoptotic nuclei were defined as those having at least one lobe of highly condensed nuclear chromatin.

Panel 4A demonstrates that the total number of cells surviving per cm$^2$ in serum containing cultures was 28,300±1,204 while only 3,700±973 cells/cm$^2$ (i.e., 13%) survived serum withdrawal. However, in these same serum-free conditions, the presence of PD 169316 protected the cell population from cell death in a dose dependent manner.

Similarly, Panel 4B demonstrates that the number of TH+ cells surviving per cm$^2$ in serum containing cultures was relatively constant, while only a relatively small proportion of TH+ cells survived serum withdrawal. However, in these same serum-free conditions, the presence of PD 169316 protected the TH+ cell population from cell death in a dose dependent manner.

Panel 4C demonstrates the ability of PD 169316 to protect cells from apoptosis. Following the various growth conditions, the cultures were stained with Hoechst 33258 DNA dye and the apoptotic cells (i.e., those containing one or more lobes of condensed nuclear chromatin) were counted. In the presence of serum, 1.4% of the cells were apoptotic after 20 hours. The removal of serum increased the number of apoptotic cells to 14%. Both 1 and 10 $\mu$M concentrations of PD 169316 reduced the rate of apoptosis to 3.4% and 1.8%, respectively. The inhibitor had no effect on the basal apoptosis (i.e., 1.4%) observed in cultures supplemented with serum.

EXAMPLE 4

Determination of Tyrosine Hydroxylase-Positive Apoptotic Cells

In this Example, experiments to study tyrosine hydroxylase-positive apoptotic cells were conducted. E15 rat ventral mesencephalic cultures were grown in F12 medium containing 5% human placental serum for 24 hrs. At that time, medium was replaced with either fresh medium or medium lacking serum in the presence or absence of PD169316 (10 $\mu$M) or SB203580 (10 $\mu$M) and cells were grown for additional 18 hrs. Next, cultures were washed with PBS and fixed for 2 min in 1% paraformaldehyde followed by further fixation in 70% ethanol in glycine buffer at $-20°$ C. for 10 min. Cultures were immunostained using a polyclonal anti-rat TH primary antibody overnight (Pel-Freez) followed by a fluorescent (FITC-conjugated) secondary antibody (Calbiochem) applied for 2 hours. Subsequently, cells were stained with a fluorescent Hoechst 33258 DNA dye (8 mg/ml, Sigma) applied for 10 min, all at room temperature. Only cells containing nuclear chromatin condensations (pyknotic nuclei) were identified as apoptotic. Cells containing intact nuclei were counted as healthy. One-way ANOVA was used to show statistical differences between treatments. Six wells were examined for each treatment. In the entire experiment, total of 5066 TH-immunoreactive neurons were examined for the nuclear chromatin condensation under a fluorescence microscope. The groups examined were:

1. + serum, n = 2595;
2. − serum, n = 269;
3. − serum + PD169316, n = 1615; and
4. − serum + SB203580, n = 587.

The results of this experiment are shown in FIG. 5. In cultures containing serum, only 8.8% dopamine neurons were apoptotic. In contrast, the removal of serum increased the number of apoptotic dopamine neurons to 32.3%. PD169316 fully blocked the increase in the apoptotic nuclear profiles resulting from serum withdrawal (p<0.001) and only 7.8% dopamine neurons were apoptotic under this protective treatment. The anti-apoptotic effect of SB203580 was also significant (p<0.001) although less dramatic than that of PD169316.

EXAMPLE 5 p38 MAP Kinase Activity Assay

In this Example, experiments to observe p38 MAP kinase activity are described. Cultured embryonic rat mesencephalon tissue are cultured as described in Example 1. After washing with ice-cold HBSS, the cells are solubilized in 400 $\mu$l of ice-cold immunoprecipitation buffer containing 10 mM Tris, pH 7.4, 1% Triton X-100, 0.5% nonidet P-40, 150 mM NaCl, 1 mM EDTA, 1 mM EGTA, 0.2 mM sodium orthovanadate, and 0.2 mM phenylmethylsulfonyl fluoride. The cell lysates are centrifuged to remove insoluble material, and 200 $\mu$g of the supernatant protein (400 $\mu$L, total volume) are incubated with 1 $\mu$g of anti-p38 antibodies for 1 hour at 4° C. followed by incubation with 30 $\mu$L of Protein G Plus/Protein Agarose for an additional hour. The immunocomplexes are pelleted and washed twice in immunoprecipitation buffer and then once in kinase wash buffer (50 mM $\beta$-glycerophosphate, 1 mM EGTA, 20 mM MgCl$_2$, 100 $\mu$M sodium orthovanadate). The protein kinase assay is initiated by the addition of 20 $\mu$L of 2× reaction buffer (50 mM $\beta$-glycerol phosphate, 1 mM EGTA, 20 mM MgCl$_2$, 100 $\mu$M sodium orthovanadate, 0.1 mg/ml ATF-2 (N-terminal half), 50 $\mu$g/ml IP20, a peptide inhibitor of cAMP dependent protein kinase, 200 $\mu$M ATP, and 0.9 mCi/ml [$^{32}$P]ATP) to 20 $\mu$L of immune complex. The reaction is allowed to proceed for 10 min at 30° C. and then terminated by the addition of 2×Laemmli sample buffer and analyzed by SDS-polyacrylamide gel electrophoresis using 12% acrylamide gels. After electrophoresis, the gels are dried and subjected to phosphoimaging (BioRad GS 100).

EXAMPLE 6

Western Immunoblotting

In this Example, Westerns used to study the expression of p38 in cells are described. Embryonic rat mesencephalon tissue was cultured as described in Example 1. The cells were scraped from the culture plates in 0.1 N NaOH. Approximately 1×10$^6$ cells from each culture treatment were solubilized in a 2×Laemmli sample buffer (Laemmli, Nature 227: 680–685 [1970]) containing 50 mM dithiothreitol. The samples were boiled for 10 min, placed on ice, and separated on 10% SDS-polyacrylamide gels. The proteins were electrophoretically transferred to polyvinylidene difluoride membranes by applying a constant voltage of 20V for approximately 16 hours. The transfer buffer consisted of 25 mM Tris, 190 mM glycine, and 20% methanol. The membranes were dried for 5 min at 37° C. and blocked for 1 hour in Tris buffered saline (pH 7.5) containing 0.1% Tween-20 and 10% nonfat dry milk. Subsequently, the membranes were washed and incubated in Tris-buffered saline (pH 7.5) containing 0.1% Tween 20, 1% nonfat dry milk, and antibodies against p38 or JNK (Santa Cruz). Immunoreactivity was detected using ECL chemiluminescent detection system (Amersham).

The levels of p38 enzyme during serum starvation with and without PD 169316 were assayed using a Western blot procedure. Results from one experiment are shown in FIGS. 6 and 7. As depicted in FIG. 6, in serum-containing cultures, the levels of p38 were unchanged over the 20 hour course of the experiment. In contrast, by 16 hours of serum withdrawal, the levels of p38 rose to 236±39% of the baseline value. By 20 hours of serum withdrawal, the levels of p38 were significantly elevated above those in serum-containing cultures (p<0.05), and reached 397±47% of the baseline value. The increase in the p38 levels observed 20 hours after serum withdrawal was reduced to the baseline value with 1 and 10 $\mu$M PD 169316 (See, FIG. 7). As shown in FIG. 7, the inhibitor (0.1 $\mu$M) did not reduce levels of p38. This low concentration of PD 169316 was also unable to rescue cells from serum-withdrawal induced death.

EXAMPLE 7

JNK Activity Assay

In this Example, experiments in which JNK activity was measured in the mesencephalic cultures prior to and 60 min following serum withdrawal in either absence or presence of PD169316 (10 µM) or SB203580 (10 µM) are described. Embryonic mesencephalic tissue was cultured as described in Example 1. Cells were solubilized for 30 min at 4° C. in 500 ml of lysis buffer (25 mM HEPES, pH 7.7, 0.1% Triton X-100, 20 mM β-glycerol phosphate, 0.3 mM NaCl, 0.1 mM sodium vanadate, 1.5 mM $MgCl_2$, 0.2 mM EDTA, 0.5 mM DTT, 2 mg/ml leupeptin and 4 mg/ml aprotinin). Lysates were centrifuiged for 5 min in a refrigerated microcentrifuge (10,000×g). Following centrifugation, 200 mg of lysate protein were incubated shaking for 2 hrs at 4° C. with GST-c-jun (1–79) immobilized to glutathione-agarose (10 ml of packed beads per sample containing 10 mg protein). The GST-c-jun agarose complexes were washed 3 times by repetitive centrifugation in 20 mM HEPES, pH 7.7, 50 mM NaCl, 2.5 mM $MgCl_2$, 0.1 mM EDTA, 0.05% Triton X-100, and then incubated for 20 min at 30° C. in 40 ml of 50 mM β-glycerolphosphate, pH 7.6, 0.1 mM sodium vanadate, 10 mM $MgCl_2$, and 20 mM ATP. The reactions were terminated with 10 µl of Laemmli sample buffer, samples were boiled, and analyzed on 12% SDS-polyacrylamide gels. The proteins were transferred to PVDF membranes and probed with antibodies against phospho-c-jun (NEB #9261) followed by the ECL detection system. Statistical analysis: data were analyzed by one-way ANOVA followed by a Student-Newman-Keuls post hoc test using InStat statistical software (GraphPad) with significance defined as $p<0.05$.

Using this protocol, it was observed that JNK activity is maintained in mesencephalic cultures grown in the presence of serum (See, FIG. 8). JNK activity was not affected during the first hour of serum withdrawal. Addition of PD 169316 (10 µM) or SB203580 (10 µM) greatly reduced JNK activity, indicating that primary rat ventral mesencephalic culture contains at least one JNK isoform that is inhibited by pyridyl imidazole compounds (See, FIG. 8).

EXAMPLE 8

TH+ Cell Survival Following Transplantation

The survival of transplanted rat embryonic mesencephalon tissue pretreated with PD169316 and SB203580 and injected into denervated rat striatum was assayed, as described below.

Lesioning median forebrain bundle: For lesioning, 20 µg of 6-OHDA was injected at two sites, AP: −2.1 mm posterior to bregma, LAT: 2.0 mm from the midline, VD: −7.8 mm below the dura; and AP: −4.3 mm posterior to bregma, LAT: 1.5 mm from the midline, VD: −7.9 mm below the dura. Once the rats successfully recovered from the lesioning procedure (7 to 10 days post 6-OHDA injection), the animals were tested to assess the extent of the striatal lesion using a methamphetamine-induced rotation (circling) behavioral test. Rats which did not show a positive result in the behavioral test were eliminated from subsequent analysis. Only animals circling above 3 rpm in ipsilateral direction were used. After lesioning, the animals were grouped such that each group mean rpm was around 8 rpm. Animals showing successful lesioning were tested again at 3 weeks and again at 6 weeks.

Transplantation: Two to six weeks passed between lesioning and transplantation. For the transplantation, one-half embryonic day 15 (E15) rat ventral mesencephalon was extruded into a strand using a 0.2 mm in diameter glass cannula made by heating a glass luer adaptor (Kimble-Kontes, Cat# 663500-0444). The tissue strand was incubated in vehicle ($Ca^{++}$/$Mg^{++}$-free Hank's Balanced Salt Solution; HBSS) or HBSS containing 10 µM PD169316 (Calbiochem) or 10 µM SB203580 (Calbiochem) for 2 hours at 37° C. in 5% carbon dioxide. Following incubation, the tissue was immediately transplanted into the denervated rat striatum. The tissue strand was drawn up into a 24 g sterile stainless steel cannula attached to a microliter syringe and stereotaxically transplanted at the following coordinates (AP 0.0 mm form bregma, LAT3.0 mm form the midline, VD-3.5 to −7.5 mm below the dura) in 4.0 µl over 4 min.

Visualization of TH+ cells: Six weeks after transplantation, all animals were sacrificed, and their brains perfused with heparinized-saline followed by 4% paraformaldehyde. The brains were sectioned on a cryotome at 40 micrometer thickness and immunostained for tyrosine hydroxylase (TH) using a polyclonal anti-rat TH antibody and a peroxidase-based ABC kit. All TH-immunoreactive neurons were counted in every third section under a microscope. Abercrombie's correction was used to estimate the total number of TH+ neurons surviving in each transplant.

Pretreatment of transplanted cells with PD169316 (10 µM) nearly doubled the number of surviving dopamine neurons per animal compared to transplanted tissue that received sham pretreatment with HBSS ($p<0.05$; Student's t-test). While the PD-treated transplants contained 3023+/−585 surviving dopamine neurons, sham-treated transplants contained only 1662+/−278 surviving dopamine neurons. Transplanted tissue treated with SB203580 contained an intermediate level of TH+ cells. All data represent the mean+/−S.E.M., where n=47 for all animal groups combined. It is contemplated that this method will find use in assessment of the potential efficacy of compounds for use in the treatment of neurodegenerative diseases, including but not limited to Parkinson's disease.

EXAMPLE 9

Effects of Transplanted Fetal Neuronal Tissue on Methamphetamine-Induced Rotation In this Example, experiments to determine the effects of transplanted fetal neuronal tissue on metharnphetamine-induced rotation were conducted as described below.

Lesioned rat striatum: Rat substantia nigra dopamine neurons were lesioned with 6-OHDA, as described in the previous Example.

Transplantation: Rats received neuronal transplants according to the protocol described above. Two to six weeks passed between lesioning and transplantation. For the transplantation, one-half embryonic day 15 (E15) rat ventral mesencephalon was extruded into a strand using a 0.2 mm in diameter glass cannula made by heating a glass luer adaptor (Kimble-Kontes, Cat# 663500–0444). The tissue strand was incubated in vehicle buffer only ($Ca^{++}$/$Mg^{++}$-free Hank's Balanced Salt Solution; HBSS) or HBSS containing 10 µM PD169316 (Calbiochem) or 10 µM SB203580 (Calbiochem) for 2 hours at 37° C., in 5% carbon dioxide. Following the incubation, the tissue was immediately transplanted into the denervated rat striatum. The tissue strand was drawn up into a 24 ga sterile stainless steel cannula attached to a microliter syringe and stereotaxically transplanted at the following coordinates (AP 0.0 mm from bregma, LAT 3.0 mm from the midline, VD−3.5 to−7.5 mm below the dura) in 4.0 μl over 4 min. In addition, a group of rats received a sham transplantation consisting of buffer vehicle only.

The following animal groups were treated as follows:
1. Transplanted with HBSS buffer vehicle only, n=9;
2. Transplanted with neuronal cell preparation receiving prior pre-treatment with buffer vehicle only, n=11;
3. Transplanted with neuronal cell preparation receiving prior pre-treatment with PD169316, n=14; and
4. Transplanted with neuronal cell preparation receiving prior pre-treatment with SB203580, n=13.

Methamphetamine treatment: At three weeks and six weeks following the transplantation, rats were injected i.p. with 5.0 mg/kg methamphetamine. Methamphetamine-injected animals were placed in vertically positioned plexi-glass drums and attached to a flexible cable that records rotations to a computer. Animals were tested for 120 minutes. During the initial 30 minutes of testing, the effects of methamphetamine developed and rotations ipsilateral to the lesion were recorded in each animal every 10 minutes during a 90 minute interval. The average ipsilateral rotations per minute (rpm) were calculated for each animal using rotational values from the previous 90 minutes of the test.

Results: Transplants of tissue pretreated with PD169316 significantly accelerated the rate of behavioral recovery when compared to the transplants of tissue pretreated with buffer only at both three and six weeks after transplantation. At six weeks, PD169316-treated group was the only group to completely stop methamphetamine-induced rotations (0.07+/−0.09 rpm). At three weeks, the reduction in rotation in the animals receiving tissue pretreated with SB203580 were significantly greater when compared to the animals transplanted with vehicle-treated tissue. All data represent the mean +/−S.E.M. Two-way ANOVA was used for the statistical analysis of the behavioral data. Values were significantly different when p<0.05. It is contemplated that this method will find use in assessment of the potential efficacy of compounds for use in the treatment of neurodegenerative diseases, including but not limited to Parkinson's disease.

EXAMPLE 10

Analysis of PD 169316-Mediated Protection Against 6-OHDA-induced Neurotoxicity In Vitro In this Example experiments to determine the ability of PD 169316 to protect against 6-OHDA neurotoxicity were conducted. Cultures of E15 rat ventral mesencephalon were grown for 5 days in medium containing 5% human placental serum as described in Example 1. At that time, the medium was changed and cultures were exposed to 50 μM 6-OHDA neurotoxin (RBI) for either 30 or 90 min. The neurotoxin was freshly prepared and the preparation contained ascorbic acid to reduce neurotoxin oxidation. Select cultures received a 30-min pretreatment with 10 μM PD169316 prior to 6-OHDA exposure. All cultures were grown for another two days in the presence or absence of PD169316. At that time, cultures were fixed in 4% paraformaldehyde and subjected to immunochemistry for detection of TH using a polyclonal anti-rat TH antibody and peroxidase-based staining kit (Vector).

The results of this experiment are shown in FIG. 12. As shown, PD169316 fully prevented dopamine cell death caused by 6-OHDA exposure. The effect was equally significant (p<0.001) regardless of the length on the neurotoxin exposure (i.e., 30 or 90 min). This finding demonstrates the in vitro efficacy of PD169316 in protecting cultured primary neurons from 6-OHDA neurotoxicity.

It is contemplated that this method will find use in assessment of the potential efficacy of compounds for use in the treatment of neurodegenerative diseases, including but not limited to Parkinson's disease.

From the above, it is clear that the present invention provides methods for preventing the death of dopamine neurons, and may be used to treat neurodegenerative diseases, including but not limited to Parkinson's disease. It is further contemplated that these methods will also find use in enhancing the survival of and protecting transplanted neurons used in the treatment of neurodegenerative diseases, including Parkinson's disease. It is further contemplated that the methods and compositions described herein will find use in investigations to identify compounds that are useful in the treatment of neurodegenerative diseases, including but not limited to Parkinson's disease.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for treating a subject, comprising the steps of:
a) providing:
   i) a subject, wherein said subject has a neurodegenerative disease, and
   ii) a composition comprising at least one pyridyl imidazole compound, wherein said pyridyl imidazole compound is selected from the group consisting of
      PD 169316; isomeric PD 169316; SB 203580; SB 202190; SB 220025; RWJ 67657;
      2-(4-Cyanophenyl)-4-(4-fluorophenyl)-5-(4-pyridyl)-1H-imidazole;
      1-Methyl-2-(4-methoxyphenyl)-4-phenyl-5-(4-pyridyl)-imidazole;
      2-(4-Cyanophenyl)-1-methyl-4-phenyl-5(4-pyridyl)imidazole;
      2-(4-Aminomethylphenyl)-1-methyl-4-phenyl-5-(4-pyridyl)-imidazole;
      4-[1-Methyl-4-phenyl-5(4-pyridyl)-imidazol-2-yl] benzoic acid, sodium salt;
      2-(4-Acetamidomethyphenyl)-1-methyl-4-phenyl-5-(4-pyridyl)imidazole;
      Methyl-4-[1-methyl-4-phenyl-5-(4-pyridyl)-imidazol-2-yl]benzoate;
      4-(4-Fluorophenyl)-N-1-hydroxy-2-(4-hydroxyphenyl)-5-(4-pyridyl)imidazole;
      4-(4-Fluorophenyl)-2-(4-hydroxyphenyl)-5-(4-pyridyl)-1H-imidazole;
      4-[4-(4-Fluorophenyl)-5-(4-pyridyl)-1H-imidazol-2-yl]benzoic acid;
      2-(4-Cyanophenyl)-4-(4-fluorophenyl)-1-N-hydroxy-5-(4-pyridyl)imidazole;
      2-(4-Aminomethylphenyl)-4-(4-fluorophenyl)-5-(4-pyridyl)-1H-imidazole;
      2-(4-Cyanophenyl)-4-(4-fluorophenyl)-N-1-hydroxy-5-(4-quinolyl)imidazole;
      2-(4-Cyanophenyl)-4-(4-fluorophenyl)-5-(4-quinolyl)-1H-imidazole;
      2-(3,5-Dibromo-4-hydroxyphenyl)-4-(4-fluorophenyl)-5-(4-pyridyl)-1H-imidazole; Ethyl 4-[4-(4-Fluorophenyl)-5-(4-pyridyl)]-1H-imidazol-2-yl]-benzoate;
2-[3,5-Dimethyl-4-hydroxy(phenyl)]-4-(4-fluorophenyl)-5-(4-pyridyl)-1H-imidazole;
4-(4-Fluorophenyl-2-(2-hydroxyphenyl)-5-(4-pyridyl)-1H-imidazole;
4-(4-Fluorophenyl)-2-(4-methylthiophenyl)-5-(4-pyridyl)-1H-imidazole; Methyl 4-[4-(4-fluorophenyl)-5-(4-pyridyl)-1H-imidazol-2-yl]-benzoate;
4-(4-Fluorophenyl)-2-(4-methylsulfonylphenyl)-5-(4-pyridyl)-1H-imidazole;
4-(4-Fluorophenyl)-2-(4-methylsulfinylphenyl)-5-(4-pyridyl)-1H-imidazole;
N,N-Dimethyl-4-[4-(4-fluorophenyl-5-(4-pyridyl)-1H-imidazol-2-yl]-benzamide;
2-[(4-N,N-Dimethyl)aminomethylphenyl]-4-(4-fluorophenyl)-5-(4-pyridyl)-1H-imidazole;
2-[4-(Dimethylamino)phenyl]-4-(4-fluorophenyl)-5-(4-pyridyl)-1H-imidazole;
4-(4-Fluorophenyl)-2-phenyl-5-(4-pyridyl)-1H-imidazole;
2-[4-(3-Dimethylaminopropoxy)phenyl]-4-(4-fluorophenyl)-5-(4-pyridyl)-1H-imidazole;
4-(4-Fluorophenyl)-2-(4-nitrophenyl)-5-(4-pyridyl)-1H-imidazole;
N,N-Dimethyl-4-[2-(4-fluorophenyl)-5-(4-pyridyl)-1H-imidazol-2-yl]-benzoyloxyacetamide;
2-(4-Aminophenyl)-4-(4-fluorophenyl)-5-(4-pyridyl)-1H-imidazole;
4-(4-Fluorophenyl)-2-(4-methanesulfonamidophenyl)-5-(4-pyridyl)-1H-imidazole;
4-[4-(4-Fluorophenyl)-5-(4-pyridyl)-1H-imidazol-2-yl]phenyl-sulfonamide;
N'-Cyano-N-4-[(fluorophenyl)-5-(4-pyridyl)-1H-imidazol-2-yl]benzylguanidine;
2-[4-(Methanesulfonamido)methylphenyl]-4-(4-fluorophenyl)-5-(4-pyridyl)-1H-imidazole;
4-(4-Fluorophenyl)-2-(4-methoxyphenyl)-5-(4-pyridyl)-1H-imidazole;
2-(4-Amino-3-iodophenyl)-4-(4-fluorophenyl)-5-(4-pyridyl)-1H-imidazole;
N-Benzyl-N-methyl-4-[4-(4-fluorophenyl-5-(4-pyridyl)-1H-imidazol-2-yl]benzamide;
2-[4-(N-Benzyl-N-methyl)aminomethylphenyl]-4-(4-fluorophenyl)-5-(4-pyridyl)-1H-imidazole;
4-(4-Fluorophenyl)-N-1-hydroxy-2-(4-methylthiophenyl)-5-(4-quinolyl)imidazole;
4-(4-Fluorophenyl)-2-(4-methylthiophenyl)-5-(4-quinolyl)-1H-imidazole;
4-(4-Fluorophenyl)-2-(4-methylsulfinylphenyl)-5-(4-quinolyl) 1H-imidazole;
4-(3-Chlorophenyl)-2-(4-methylsulfinylphenyl)-5-(4-pyridyl)-1H-imidazole;
4-(3-Chlorophenyl)-N-1-hydroxy-2-(4-methylthio-phenyl)-5-(4-pyridyl)-1H-imidazole;
4-(3-Chlorophenyl)-2-(4-methylthiophenyl)-5-(4-pyridyl)-1H-imidazole;
4-(4-Fluorophenyl)-2-(4-formamidomethylphenyl)-5-(4-pyridyl)-1H-imidazole;
4-[4-(4-Fluorophenyl)-5-(4-pyridyl)-1H-imidazol-2-yl]-benzohydroxamic acid;
O-Benzyl-4-[4-(4-Fluorophenyl)-5-(4-pyridyl)-1H-imidazol-2-yl]-benzohydroxamic acid;
4-[4-(4-Fluorophenyl)-5-(4-pyridyl)-1H-imidazol-2-yl]benzamidoxime;
N''-Methyl-N'-cyano-N-[4-(4-fluorophenyl)-5-(4-pyridyl)-1H-imidazol-2-yl]-benzylguanidine;
N-1-Hydroxy-4-(3-methoxyphenyl)-2-(4-methylthiophenyl)-5-(4-pyridyl)-1H-imidazole;4-(3-ethoxyphenyl)-2-(4-methylthiophenyl)-5-(4-pyridyl)imidazole;
4-(3-Methoxyphenyl)-2-(4-methylsulfinylphenyl)-5-(4-pyridyl)-1H-imidazole;
Morpholino-4-[4-(4-fluorophenyl)-5-(4-pyridyl)-1H-imidazol-2-yl]benzamide;
4-(4-Fluorophenyl)-5-[4-(2-methylpyridyl)]-2-(4-methylthiophenyl)-1H-imidazole;
4-(4-Fluorophenyl)-5-[4-(2-methylpyridyl)]-2-(4-methylsulfinylphenyl)-1H-imidazole;
4-(4-Fluorophenyl)-N-1-hydroxy-5-(4-pyrimidinyl)imidazole;
4-(4-Fluorophenyl)-2-(4-methylthiophenyl)-5-(4-pyrimidinyl)-1H-imidazole;
4-(4-Fluorophenyl)-2-(4-methylsulfinylphenyl)-5-(4-pyrimidinyl)-1H-imidazole;
4-(4-Fluorophenyl)-2-(4-methylsulfonylphenyl)-5-(4-pyrimidinyl)-1H-imidazole;
4-(4-Fluorophenyl)-2-(4-Morpholinomethylphenyl)-5-(4-pyridyl)-1H-imidazole;
4-(4-Fluorophenyl)-2-(4-hydroxymethyl)-5-(4-pyridyl)-1H-imidazole;
4-[4-(4-Fluorophenyl)-5-(4-pyridyl)-1H-imidazol-2-yl]-benzaldehyde;
4-(2-Methoxyphenyl)-2-(4-methylsulfinylphenyl)-5-(4-pyridyl)-1H-imidazole;
N-1-Hydroxy-4-(2-methoxyphenyl)-2-(4-methylthio-phenyl)-5-(4-pyridyl)imidazole;
4-(2-Methoxyphenyl)-2-(4-methylthiophenyl)-5-(4-pyridyl)-1H-imidazole;
3-[4-(4-Fluorophenyl)-5-(4-pyridyl)-1H-imidazol-2-yl]phenyl-5-methyl-4,5-dihydro-1,2,4-oxadiazole; 3-[4-(4-Fluorophenyl)-5-(4-pyridyl)-1H-imidazol-2-yl]phenyl-5-methyl-1,2,4-oxadiazole;
4-(3-Aminophenyl)-2-(4-methylthiophenyl)-5-(4-pyridyl)-1H-imidazole;
N-1-Hydroxy-2-(4-methylthiophenyl)-4-(3-nitrophenyl)-5-(4-pyridyl)imidazole;
2-(4-Methylthiophenyl)-4-(3-nitrophenyl)-5-(4-pyridyl)-1H-imidazole;
4-(3-Methanesulfonamidophenyl)-2-(4-methylthiophenyl)-5-(4-pyridyl)-1H-imidazole;
3-[4-(4-Fluorophenyl)-5-(4-pyridyl)-1H-imidazol-2-yl]phenyl-1,2,4-oxadiazol-5(4H)-one;
4-(3-Acetamidophenyl)-2-(4-methylthiophenyl)-5-(4-pyridyl)-1H-imidazole;
4-(4-Fluorophenyl)-1-N-hydroxy-5-[4-(2-methylpyridyl)]-2-(4-methylthiophenyl)-imidazole;
3-[4-(4-Fluorophenyl)-5-(4-pyridyl)-1H-imidazol-2-yl]-phenyl-5,5-dimethyl-4,5-dihydro-1,2,4-oxadiazole;
N-Hydroxy-N-1-[4-[4-(4-fluorophenyl)5-(4-pyridyl)-1H-imidazol-2-yl]phenyl]-ethyl]urea;
N-Hydroxy-N-[4-[4-(4-fluorophenyl)-5-(4-pyridyl)-1H-imidazol-2-yl]phenyl]-methyl urea;
4-(3-Methylthiophenyl)-2-(4-morpholinomethylphenyl)-5-(4-pyridyl)-1H-imidazole;
4-(3-Methylsulfinylphenyl)-2-(4-morpholinomethylphenyl)-5-(4-pyridyl)-1H-imidazole;

4-(3-Methanesulfonamidophenyl)-2-(4-methylsulfinylpheny )-5-(4-pyridyl)-1H-imidazole 2-(4-Ethylthiophenyl)-4-(4-fluorophenyl)-5-(4-pyridyl)-1H-imidazole;

4-(4-Fluorophenyl)-2-[(4-(4-methyl-1-piperzinyl)-sulfonyl-phenyl]-5-(4-pyridyl) 1H-imidazole;

4-(4-Fluorophenyl)-2-[4-(N-methylmethanesulfonamido)-methylphenyl]-5-(4-pyridyl)-1H-imidazole; Diethyl-[1-methyl-4-phenyl-5-(4-pyridyl)-imidazol-2-yl]-methoxy methylphosphonate;

4-(4-Fluorophenyl)-2-(4-methylthiophenyl)-5-(4-pyridyl)-1H-imidazole;

4-(4-Fluorophenyl)-2-(3-methylthiophenyl)-5-(4-pyridyl)-1H-imidazole;

4-(4-Fluorophenyl)-2-(3-methylsulfinylphenyl)-5-(4-pyridyl)-1H-imidazole;

4-(4-Fluorophenyl)-2-(4-methoxyphenyl)-5-(4-pyridyl)imidazole;

4-(4-Fluorophenyl)-2-(4-methylsulfinylphenyl)-1-(N-morpholinopropyl)-5-(4-pyridyl)-imidazole; 4-(4-Fluorophenyl)-2-(4-methylthiophenyl)-1-(N-morpholinopropyl)-5-(4-pyridyl)-imidazole; 4-(4-Fluorophenyl)-2-(4-methylsulfonylphenyl)-1-(N-morpholinopropyl)-5-(4-pyridyl)imidazole;4-(4-Fluorophenyl)-1-(methylthio-1-propyl)-2-([4-N-morpholinomethyl]phenyl)-5-(4-pyridyl) imidazole;

4-(4-Fluorophenyl)-1-(methylsulfinyl-1-propyl)-2-([4N-morpholinomethyl]phenyl)-5-(4-pyridyl) imidazole; 4-(4-Fluorophenyl)-1-(methylsulfonyl-1-propyl)-2-([4-N-morpholinomethyl]phenyl)-5-(4-pyridyl) imidazole; and pharmaceutically acceptable salts thereof; and b) administering said composition to said subject under conditions such that said neurodegenerative disease in said subject is ameliorated.

2. The method of claim 1, wherein said neurodegenerative disease is selected from the group consisting of Parkinson's disease, Huntington's disease, Alzheimer's disease and amyotrophic lateral sclerosis.

3. The method of claim 1, wherein said administering is orally.

4. The method of claim 1, wherein said composition is a therapeutic composition.

5. The method of claim 1, wherein said subject is a human.

6. The method of claim 5, wherein said human is a recipient of transplanted cells.

7. The method of claim 6, wherein said administering step further comprises the of administering said composition to said subject under conditions such that the survival and transplanted cells in said human is improved.

8. The method of claim 6, wherein said administering step further comprises the of administering said composition to said subject under conditions such that the function of said transplanted cells in said human is improved.

9. The method of claim 6, wherein said administering step further comprises the of administering said composition to said subject under conditions such that the survival function of said transplanted cells in said human is improved.

10. The method of claim 1, wherein said subject is a non-human animal.

11. A method for inhibiting p38 and c-jun-N-terminal kinase activities, comprising the steps of:

a) providing:

i) a sample comprising p38 and c-jun-N-terminal kinase activities, and ii) a pyridyl imidazole compound, wherein said pyridyl imidazole is selected from the group consisting of PD 169316; isomeric PD 169316; SB 203580; SB 202190; SB 220025; RWJ 67657;

2-Cyanophenyl)-4-(4-fluorophenyl)-5-(4-pyridyl)-1H-imidazole;

1-Methyl-2-(4-methoxyphenyl)-4-phenyl-5-(4-pyridyl)-imidazole;

2-(4-Cyanophenyl)-1-methyl-4-phenyl-5(4-pyridyl) imidazole;

2-(4-Aminomethylphenyl)-1-methyl-4-phenyl-5-(4-pyridyl)-imidazole;

4[1-Methyl-4-phenyl-5(4-pyridyl)-imidazol-2-yl] benzoic acid, sodium salt;

2-(4-Aminomethylphenyl)-1-methyl-4-phenyl-5-(4-pyridyl)imidazole;

Methyl-4-[1-methyl-4-phenyl-5-(4-pyridyl)-imidazol-2-yl]benzoate;

4-(4-Fluorophenyl)-N-1-hydroxy-2-(4-hydroxyphenyl)-5-(4-pyridyl)imidazole;

4-(4-Fluorophenyl)-2-(4-hydroxyphenyl)-5-(4-pyridyl)-1H-imidazole;

4-[4-(4-Fluorophenyl)-5-(4-pyridyl)-1H-imidazol-2-yl]benzoic acid;

2-(4-Cyanophenyl)-4-(4-fluorophenyl)-1-N-hydroxy-5-(4-pyridyl)imidazole;

2-(4-Aminomethylphenyl)-4-(4-fluorophenyl)-5-(4-pyridyl)-1H-imidazole;

2-(4-Cyanophenyl)-4-(4-fluorophenyl)-N-1-hydroxy-5-(4-quinolyl)imidazole;

2-(4-Cyanophenyl)-4-(4-fluorophenyl)-5-(4-quinolyl)-1H-imidazole;

2-(3,5-Dibromo-4-hydroxyphenyl)-4-(4-fluorophenyl)-5-(4-pyridyl)-1H-imidazole;

Ethyl4-[4-(4-Fluorophenyl)-5-(4-pyridyl)]-1H-imidazol-2-yl]-benzoate;

2-[3,5-Dimethyl-4-hydroxy(phenyl)]-4-(4-fluorophenyl)-5-(4-pyridyl)-1H-imidazole;

4-(4-Fluorophenyl-2-(2-hydroxyphenyl)-5-(4-pyridyl)-1H-imidazole;

4-(4-Fluorophenyl)-2-(4-methylthiophenyl)-5-(4-pyridyl)-1H-imidazole;

Methyl4-[4-(4-fluorophenyl)-5-(4-pyridyl)-1H-imidazol-2-yl]-benzoate;

4-(4-Fluorophenyl)-2-(4-methylsulfonylphenyl)-5-(4-pyridyl)-1H-imidazole;

4-(4-Fluorophenyl)-2-(4-methylsulfinylphenyl)-5-(4-pyridyl)1H-imidazole;

N,N-Dimethyl-4-[4-(4-fluorophenyl-5-(4-pyridyl)-1H-imidazol-2-yl]-benzamide;

2-[(4-N,N-Dimethyl)aminomethylphenyl]-4-(4-fluorophenyl)-5-(4-pyridyl)-1H-imidazole;

2-[4-(Dimethylamino)phenyl]-4-(4-fluorophenyl)-5-(4-pyridyl)-1H-imidazole;

4-(4-Fluorophenyl)-2-phenyl-5-(4-pyridyl)-1H-imidazole;

2-[4-(3-Dimethylaminopropoxy)phenyl]-4-(4-fluorophenyl)-5-(4-pyridyl)-H-imidazole;

4-(4-Fluorophenyl)-2-(4-nitrophenyl)-5-(4-pyridyl)-1H-imidazole;

N,N-Dimethyl-4-[2-(4-fluorophenyl)-5-(4-pyridyl)-1H-imidazol-2-yl]-benzoyloxyacetamide;

2-(4-Aminophenyl)-4-(4-fluorophenyl)-5-(4-pyridyl)-1H-imidazole;

4-(4-Fluorophenyl)-2-(4-methanesulfonamidophenyl)-5-(4-pyridyl)-1H-imidazole;

4-[4-(4-Fluorophenyl)-5-(4-pyridyl)-1H-imidazol-2-yl]phenyl-sulfonamide;
N'-Cyano-N-4-[4-(fluorophenyl)-5-(4-pyridyl)-1H-imidazol-2-yl]benzylguanidine;
2-[4-(Methanesulfonamido)methylphenyl]-4-(4-fluorophenyl)-5-(4-pyridyl)-1H-imidazole;
4-(4-Fluorophenyl)-2-(4-methoxyphenyl)-5-(4-pyridyl)-1H-imidazole;
2-(4-Amino-3-iodophenyl)-4-(4-fluorophenyl)-5-(4-pyridyl)-1H-imidazole;
N-Benzyl-N-methyl-4-[4-(4-fluorophenyl-5-(4-pyridyl)-1H-imidazol-2-yl]benzamide;
2-[4-(N-Benzyl-N-methy)aminomethylphenyl]-4-(4-fluorophenyl)-5-(4-pyridyl)-1H-imidazole;
4-(4-Fluorophenyl-1-hydroxy-2-(methylthiophenyl)-5-(4(quinoly)imidazole;
4-(4Fluorophenyl)-2-(4-methylthiophenyl)-5-(4-(quinoly)-1H-imidazole;
4-(4Fluorophenyl)-2-(4-methylsufinylphenyl)-5-(4-(quinoly)-1H-imidazole;
4-(3-Chlorophenyl-2-(4-methylsufinylphenyl)-5-(4-(pyridyl)-1H-imidazole;
4-(3-Chlorophenyl)-N-1-hydroxy2-(4-methylthio-phenyl)5-(4)-1H-imidazole;
4-(3-Chlorophenyl)-2-(4-methylthiophenyl)-5-(4-(pyridyl)-1H-imidazole;
4-(4Fluorophenyl)-2-(4-formamidomethylphenyl)-5-(4-(pyridyl)-1H-imidazole;
4-[4-(4-Fluorophenyl-5-(4-pyridyl)-1H-imidazol-2-yl]-benzohydroxamic acid;
O-Benzyl-4-[4-(4-Fluorophenyl)-5-(4-pyridyl)-1H-imidazol-2-yl]-benzohydroxamic acid;
4[4-(Fluorophenyl)-5-(4-pyridyl)-1H-imidazol-2-yl]-benzohydoxime;
N''-Methyl-N'-canyo-N-[4-(4-fluorophenyl)-5-(4-pyridyl)-1H-imidazol-2-yl]-benzylguanidine;
N-1-Hydroxy-4-(3-methoxyphenyl)-2-(4-methylthiophenyl)-5-(4-pyridyl)-1H-imidazol;
4-(3-Methoxyphenyl)-2-(4-methylthiophenyl)-5-(4-pyridyl)imidazole;
4-(3-Methoxyohenyl)-2-(4-methylthiophenyl)-5-(4-pyridyl)-1H-imidazole;
Morpholino-4-[4-(4-fluorophenyl)-5-(4-pyridyl)-1H-imidazol-2-yl]benzomde;
4-(4-Fluorophenyl)-5-[(4-(2-(4-methylthiophenyl)-1H-imidozole;
4-(4-Fluorophenyl)-5-[(4-(2-methylpyridyl)]-2-(4-methylsulfinylphenyl)-1H-imidozole;
4-(4-fluorophenyl)-N-1-hydroxy-5-(4pyrimidinyl)-imidazole;
4-(4-Fluorophenyl)-2-(4-methylthiophenyl)-5-(4-pyrimidinyl)-1H-imidozole;
4-(4-Fluorophenyl)-2-(4-methylsulfinylphenyl)-5-(4-pyrimidinyl)-1H-imidozole;
4-(4-Fluorophenyl)-2-(4-methylsulfinylphenyl)-5-(4-pyrimidinyl)-1H-imidozole;
4-(4-Fluorophenyl)-2-(4-Morpholinomethylphenyl)-5-(4-pyridyl)-1H-imidozole;
4-(4-Fluorophenyl)-2-(4-hydroxymethyl)-5-(4-pyridyl)-1H-imidozole;
4-[4-(4-Fluorophenyl-5-(4-pyridyl)-1H-imidazol-2-yl]-benzaldehyde;
4-(2-Methoxyohenyl)-2-(4-methylsulfinylphenyl)-5-(4-pyridyl)-1H-imidazole;
N-1-Hydroxy-4-(2-methoxyphenyl)-2-(4-methylthio-phenyl)-5-(4-pyridyl)imidazole;
4-(2-Methoxyohenyl)-2-(4-methylthiophenyl)-5-(4-pyridyl)-1H-imidazole;
3-[4-(4-Fluorophenyl-5-(4-pyridyl)-1H-imidazol-2-yl]phenyl-5-methyl-4, 5-dihydro-1,2,4-oxadiaxole;
3-[4-(4-Fluorophenyl-5-(4-pyridyl)-1H-imidazol-2-yl]phenyl-5-methyl-1,2,4-oxadiazole;
4-(3-Aminophenyl)-2-(4-methylthiophenyl)-5-(4-pyridyl)-1H-imidazole;
N-1-Hydroxy-2-(4-methylthiophenyl)-4-(3-nitrophenyl)-5-(4-pyridyl)imidazole;
2-(4-Methylthiophenyl)-4-(3-nitrophenyl)-5-(4-pyridyl)-1H-imidazole;
4-(3-Methanesulfonamidophenyl)-2-(4-methylthiophenyl)-5 (4-pyridyl)-1H-imidazole;
3-[4-(4-Fluorophenyl)-5-(4-pyridyl)-1H-imidazol-2-yl]phenyl-1,2,4-oxadiazol-5-(4H)-one;
4-(3-Acetamidophenyl)-2-(4-methylthiophenyl)-5-(4-pyridyl)-1H-imidazole;
4-(4-Fluorophenyl)-1-N-hydroxy-5-[4-(2-methylpyridyl)]-2-(4-methylthiophenyl)imidazole;
3-[4-(4-Fluorophenyl)-5-(4-pyridyl)-1H-imidazol-2-yl]-phenyl-5,5-dimethyl-4,5-dihydro-1,2,4-oxadiazole;
N-Hydroxy-N-1-[4-[4-(4-fluorophenyl)5-(4-pyridyl)-1H-imidazol-2-yl]phenyl-ethyl]urea;
N-Hydroxy-N-[4-[4-(4-fluorophenyl)-5-(4-pyridyl)-1H-imidazol-2-yl]phenyl]-methyl urea;
4-(3-Methylthiophenyl)-2-(4-morpholinomethylphenyl)-5-(4-pyridyl)-1H-imidazole;
4-(3-Methylsulfinylphenyl)-2-(4-morpholinomethylphenyl)-5-(4-pyridyl)-1H-imidazole;
4-(3-Methanesulfonamidophenyl)-2-(4-methylsulfinylphenyl)-5-(4-pyridyl)-1H-imidazole
2-(4-Ethylthiophenyl)-4-(4-fluorophenyl)-5-(4-pyridyl)-1H-imidazole;
2-(4-Ethylsulfinylphenyl)-4-(4-fluorophenyl)-5-(4-pyridyl)-1H-imidazole;
4-(4-Fluorophenyl)-2-[(4-(4-methyl-1-piperzinyl)-sulfonyl-phenyl]-5-(4-pyridyl)-1H-imidazole;
4-(4-Fluorophenyl)-2-[4-(N-methylmethanesulfonamido)-methylphenyl]-5-(4-pyridyl)-1H-imidazole; Diethyl-[1-methyl-4-phenyl-5-(4-pyridyl)-imidazol-2-yl]-methoxy methylphosphonate;
4-(4-Fluorophenyl)-2-(4-methylthiophenyl)-5-(4-pyridyl)-1H-imidazole;
4-(4-Fluorophenyl)-2-(3-methylthiophenyl)-5-(4-pyridyl)-1H-imidazole;
4-(4-Fluorophenyl)-2-(3-methylsulfinylphenyl)-5-(4-pyridyl)-1H-imidazole;
4-(4-Fluorophenyl)-2-(4-methoxyphenyl)-5-(4-pyridyl)imidazole;
4-(4-Fluorophenyl)-2-(4-methylsulfinylphenyl)-1-(N-morpholinopropyl)-5-(4-pyridyl)-imidazole;
4-(4-Fluorophenyl)-2-(4-methylthiophenyl)-1-(N-morpholinopropyl)-5-(4-pyridyl)-imidazole;
4-(4-Fluorophenyl)-2-(4-methylsulfonylphenyl)-1-(N-morpholinopropyl)-5-(4-pyridyl)imidazole;
4-(4-Fluorophenyl)-1-(methylthio-1-propyl)-2-([4-N-morpholinomethyl]phenyl)-5-(4-pyridyl)imidazole;
4-(4-Fluorophenyl)-1-(methylsulfinyl-1-propyl)-2-([4N-morpholinomethyl]phenyl)-5-(4-pyridyl)imidazole;

4-(4-Fluorophenyl)-1-(methylsulfonyl-1-propyl)-2-
([4-N-morpholinomethyl]phenyl)-5-(4-pyridyl)
imidazole; and pharmaceutically acceptable salts
thereof; and b) exposing said sample to said compound under conditions such that said p38 and c-jun-N-terminal kinase activities are inhibited.

12. A method for preventing apoptosis of dopamine neurons, comprising the steps of:
 a) providing:
  i) dopamine neurons, wherein said dopamine neurons are selected from the group consisting of transplanted dopamine neurons and endogenous dopamine neurons; and
  ii) a composition comprising at least one pyridyl imidazole, wherein said pyridyl imidazole compound is selected from the group consisting of PD 169316; isomeric PD 169316; SB 203580; SB 202190; SB 220025; RWJ 67657;
   2-(4-Cyanophenyl)-4-(4-fluorophenyl)-5-(4-pyridyl)-1H-imidazole;
   1-Methyl-2-(4-methoxyphenyl)-4-phenyl-5-(4-pyridyl)-imidazole;
   2-(4-Cyanophenyl)-1-methyl-4-phenyl-5(4-pyridyl) imidazole;
   2-(4-Aminomethylphenyl)-1-methyl-4-phenyl-5-(4-pyridyl)-imidazole;
   4-[1-Methyl-4-phenyl-5(4-pyridyl)-imidazol-2-yl] benzoic acid, sodium salt;
   2-(4-Acetamidomethyphenyl)-1-methyl-4-phenyl-5-(4-pyridyl)imidazole;
   Methyl-4-[1-methyl-4-phenyl-5-(4-pyridyl)-imidazol-2-yl]benzoate;
   4-(4-Fluorophenyl)-N-1-hydroxy-2-(4-hydroxyphenyl)-5-(4-pyridyl)imidazole;
   4-(4-Fluorophenyl)-2-(4-hydroxyphenyl)-5-(4-pyridyl)-1H-imidazole;
   4-[4-(4-Fluorophenyl)-5-(4-pyridyl)-1H-imidazol-2-yl]benzoic acid;
   2-(4-Cyanophenyl)-4-(4-fluorophenyl)-1-N-hydroxy-5-(4-pyridyl)imidazole;
   2-(4-Aminomethylphenyl)-4-(4-fluorophenyl)-5-(4-pyridyl)-1H-imidazole;
   2-(4-Cyanophenyl)-4-(4-fluorophenyl)-N-1-hydroxy-5-(4-quinolyl)imidazole;
   2-(4-Cyanophenyl)-4-(4-fluorophenyl)-5-(4-quinolyl)-1H-imidazole;
   2-(3,5-Dibromo-4-hydroxyphenyl)-4-(4-fluorophenyl)-5-(4-pyridyl)-1H-imidazole;
   Ethyl4-[4-(4-Fluorophenyl)-5-(4-pyridyl)]-1H-imidazol-2-yl]-benzoate;
   2-[3,5-Dimethyl-4-hydroxy(phenyl)]-4-(4-fluorophenyl)-5-(4-pyridyl)-1H-imidazole;
   4-(4-Fluorophenyl-2-(2-hydroxyphenyl)-5-(4-pyridyl)-1H-imidazole;
   4-(4-Fluorophenyl)-2-(4-methylthiophenyl)-5-(4-pyridyl)-1H-imidazole;
   Methyl 4-[4-(4-fluorophenyl)-5-(4-pyridyl)-1H-imidazol-2-yl]-benzoate;
   4-(4-Fluorophenyl)-2-(4-methylsulfonylphenyl)-5-(4-pyridyl)-1H-imidazole;
   4-(4-Fluorophenyl)-2-(4-methylsulfinylphenyl)-5-(4-pyridyl)-1H-imidazole;
   N,N-Dimethyl-4-[4-(4-fluorophenyl-5-(4-pyridyl)-1H-imidazol-2-yl]-benzamide;
   2-[(4-N,N-Dimethyl)aminomethylphenyl]-4-(4-fluorophenyl)-5-(4-pyridyl)-1H-imidazole;
   2-[4-(Dimethylamino)phenyl]-4-(4-fluorophenyl)-5-(4-pyridyl)-1H-imidazole;
   4-(4-Fluorophenyl)-2-phenyl-5-(4-pyridyl)-1H-imidazole;
   2-[4-(3-Dimethylaminopropoxy)phenyl]-4-(4-fluorophenyl)-5-(4-pyridyl)-1H-imidazole;
   4-(4-Fluorophenyl)-2-(4-nitrophenyl)-5-(4-pyridyl)-1H-imidazole;
   N,N-Dimethyl-4-[2-(4-fluorophenyl)-5-(4-pyridyl)-1H-imidazol-2-yl]-benzoyloxyacetamide;
   2-(4-Aminophenyl)-4-(4-fluorophenyl)-5-(4-pyridyl)-1H-imidazole;
   4-(4-Fluorophenyl)-2-(4-methanesulfonamidophenyl)-5-(4-pyridyl)-1H-imidazole;
   4-[4-(4-Fluorophenyl)-5-(4-pyridyl)-1H-imidazol-2-yl]phenyl-sulfonamide;
   4'-Cyano-N-4-[4-(fluorophenyl)-5-(4-pyridyl)-1H-imidazol-2-yl]benzylguanidine;
   4-[4-(Methanesulfonamido)methylphenyl]-4-(4-fluorophenyl)-5-(4-pyridyl)-1H-imidazole;
   4-(4-Fluorophenyl)-2-(4-methoxyphenyl)-5-(4-pyridyl)-1H-imidazole;
   2-(4-Amino-3-iodophenyl)-4-(4-fluorophenyl)-5-(4-pyridyl)-1H-imidazole;
   N-Benzyl-N-methyl-4-[4-(4-fluorophenyl-5-(4-pyridyl)-1H-imidazol-2-yl]benzamide;
   2-[4-(N-Benzyl-N-methyl)aminomethylphenyl]-4-(4-fluorophenyl)-5-(4-pyridyl)-1H-imidazole;
   4-(4-Fluorophenyl)-N-1-hydroxy-2-(4-methylthiophenyl)-5-(4-quinolyl)imidazole;
   4-(4-Fluorophenyl)-2-(4-methylthiophenyl)-5-(4-quinolyl)-1H-imidazole;
   4-(4-Fluorophenyl)-2-(4-methylsulfinylphenyl)-5-(4-quinolyl)-1H-imidazole;
   4-(3-Chlorophenyl)-2-(4-methylsulfinylphenyl)-5-(4-pyridyl)-1H-imidazole;
   4-(3-Chlorophenyl)-N-1-hydroxy-2-(4-methylthiophenyl)-5-(4-pyridyl)-1H-imidazole;
   4-(3-Chlorophenyl)-2-(4-methylthiophenyl)-5-(4-pyridyl)-1H-imidazole;
   4-(4-Fluorophenyl)-2-(4-formamidomethylphenyl)-5-(4-pyridyl)-1H-imidazole;
   4-[4-(4-Fluorophenyl)-5-(4-pyridyl)-1H-imidazol-2-yl]-benzohydroxamic acid;
   O-Benzyl-4-[4-(4-Fluorophenyl)-5-(4-pyridyl)-1H-imidazol-2-yl]-benzohydroxamic acid;
   4-[4-(4-Fluorophenyl)-5-(4-pyridyl)-1H-imidazol-2-yl]benzamidoxime;
   N"-Methyl-N'-cyano-N-[4-(4-fluorophenyl)-5-(4-pyridyl)-1H-imidazol-2-yl]-benzylguanidine;
   N-1-Hydroxy-4-(3-methoxyphenyl)-2-(4-methylthiophenyl)-5-(4-pyridyl)-1H-imidazole;
   4-(3M ethoxyphenyl)-2-(4-methylthiophenyl)-5-(4-pyridyl)imidazole;
   4-(3-Methoxyphenyl)-2-(4-methylsulfinylphenyl)-5-(4-pyridyl)-1H-imidazole;
   Morpholino-4-[4-(4-fluorophenyl)-5-(4-pyridyl)-1H-imidazol-2-yl]benzamide;
   4-(4-Fluorophenyl)-5-[4-(2-methylpyridyl)]-2-(4-methylthiophenyl)-1H-imidazole;
   4-(4-Fluorophenyl)-5-[4-(2-methylpyridyl)]-2-(4-methylsulfinylphenyl)-1H-imidazole;
   4-(4-Fluorophenyl)-N-1-hydroxy-5-(4-pyrimidinyl)-imidazole;
   4-(4-Fluorophenyl)-2-(4-methylthiophenyl)-5-(4-pyrimidinyl)-1H-imidazole;

4-(4-Fluorophenyl)-2-(4-methylsulfinylphenyl)-5-(4-pyrimidinyl)-1H-imidazole;
4-(4-Fluorophenyl)-2-(4-methylsulfonylphenyl)-5-(4-pyrimidinyl)-1H-imidazole;
4-(4-Fluorophenyl)-2-(4-Morpholinomethylphenyl)-5-(4-pyridyl)-1H-imidazole;
4-(4-Fluorophenyl)-2-(4-hydroxymnethyl)-5-(4-pyridyl)-1H-imidazole;
4-[4-(4-Fluorophenyl)-5-(4-pyridyl)-1H-imidazol-2-yl]-benzaldehyde;
4-(2-Methoxyphenyl)-2-(4-methylsulfinylphenyl)-5-(4-pyridyl)-1H-imidazole;
N-1-Hydroxy-4-(2-methoxyphenyl)-2-(4-methylthio-phenyl)-5-(4-pyridyl)imidazole;
4-(2-Methoxyphenyl)-2-(4-methylthiophenyl)-5-(4-pyridyl)-1H-imidazole;
3-[4-(4-Fluorophenyl)-5-(4-pyridyl)-1H-imidazol-2-yl]phenyl-5-methyl-4,5-dihydro-1,2,4-oxadiazole;
3-[4-(4-Fluorophenyl)-5-(4-pyridyl)1H-imidazol-2-yl]phenyl-5-methyl-1,2,4-oxadiazole;
4-(3-Aminophenyl)-2-(4-methylthiophenyl)-5-(4-pyridyl)-1H-imidazole;
N-1-Hydroxy-2-(4-methylthiophenyl)-4-(3-nitrophenyl)-5-(4-pyridyl)imidazole;
2-(4-Methylthiophenyl)-4-(3-nitrophenyl)-5-(4-pyridyl)-1H-imidazole;
4-(3-Methanesulfonamidophenyl)-2-(4-methylthiophenyl)-5-(4-pyridyl)-1H-imidazole;
3[4-(4-Fluorophenyl)-5-(4-pyridyl)1H-imidazol-2-yl]phenyl-1,2,4-oxadiazol-5-(4H)-one;
4-(3-Acetamidophenyl)-2-(4-methylthiophenyl)-5-(4-pyridyl)-1H-imidazole;
4-(4-Fluorophenyl)-1-N-hydroxy-5-[4-(2-methylpyridyl)]-2-(4-methylthiophenyl)-imidazole;
3[4-(4-Fluorophenyl)-5-(4-pyridyl)1H-imidazol-2-yl]-phenyl-5,5-dimethyl-4,5-dihydro-1,2,4oxadiazole;
N-Hydroxy-N-1-[4-[4-(4-fluorophenyl)5-(4-pyridyl)-1H-imidazol-2-yl]phenyl]ethyl]urea;
N1-Hydroxy-N-[4-[4-(4-fluorophenyl)-5-(4-pyridyl)-1H-imidazol-2-yl]phenyl]-methyl urea;
4-(3-Methylthiophenyl)-2-(4-morpholinomethylphenyl)-5-(4-pyridyl)-1H-imidazole;
4-(3-Methylsulfinylphenyl)-2-(4-morpholinomethylphenyl)-5-(4-pyridyl)-1H-imidazole;
4-(3-Methanesulfonamidophenyl)-2-(4-methylsulfinylphenyl)-5-(4-pyridyl)-1H-imidazole
2-(4-Ethylthiophenyl)-4-(4-fluorophenyl)-5-(4-pyridyl)-1H-imidazoie;
2-(4-Ethylsulfinylphenyl)-4-(4-fluorophenyl)-5-(4-pyridyl)-1H-imidazole;
4-(4-Fluorophenyl)-2-[(4-(4-methyl-1-piperzinyl)-sulfonyl-phenyl]-5,1-(4-pyridyl)-1H-imidazole;
4-(4-Fluorophenyl)-2-[4-(N-methylmethanesulfonamido)-methylphenyl]-5-(4-pyridyl)-H-imidazole;
Diethyl-[1-methyl-4-phenyl-5-(4-pyridyl)-imidazol-2-yl]-methoxy methylphosphonate;
4-(4-Fluorophenyl)-2-(4-methylthiophenyl)-5-(4-pyridyl)-1H-imidazole;
4-(4-Fluorophenyl)-2-(3-methylthiophenyl)-5-(4-pyridyl)-1H-imidazole;
4-(4-Fluorophenyl)-2-(3-methylsulfinylphenyl)-5-(4-pyridyl)-1H-imidazole;
4-(4-Fluorophenyl)-2-(4-methoxyphenyl)-5-(4-pyridyl)imidazole;
4-(4-Fluorophenyl)-2-(4-methylsulfinylphenyl)-1-(N-morpholinopropyl)-5-(4-pyridyl)-imidazole;
4-(4-Fluorophenyl)-2-(4-methylthiophenyl)-1-(N-morpholinopropyl)-5-(4-pyridyl)-imidazole;
4-(4-Fluorophenyl)-2-(4-methylsulfonylphenyl)-1-(N-morpholinopropyl)-5-(4-pyridyl)imidazole;
4-(4-Fluorophenyl)-1-(methylthio-1-propyl)-2-([4-N-morpholinomethyl]-phenyl)-5-(4-pyridyl)imidazole;
4-(4-Fluorophenyl)-1-(methylsulfinyl-1-propyl)-2-([4N-morpholinomethyl]phenyl)-5-(4-pyridyl)imidazole;
4-(4-Fluorophenyl)-1-(methylsulfonyl-1-propyl)-2-[4-N-morpholinomethyl]phenyl)-5-(4-pyridyl)imidazole; and pharmaceutically acceptable salts thereof; and b) exposing said composition to said dopamine neurons under conditions such that apoptosis of said dopamine neurons is prevented.

13. The method of claim 12, further comprising the step of implanting said dopamine neurons in a subject, and wherein said exposing step occurs before said implanting step.

14. The method of claim 12, further comprising the step of implanting said dopamine neurons in a subject, and wherein said exposing step occurs after said implanting step.

15. The method of claim 12, further comprising the step of implanting said dopamine neurons in a subject, and wherein said exposing step occurs before and after said implanting step.

* * * * *